United States Patent
Wraith

(10) Patent No.: US 8,445,448 B2
(45) Date of Patent: May 21, 2013

(54) FVIII PEPTIDES AND THEIR USE IN TOLERISING HAEMOPHILIACS

(75) Inventor: David Wraith, Bristol (GB)

(73) Assignee: Apitope International NV, Diepenbeck (BE)

( * ) Notice: Subject to any disclaimer, the term of this patent is extended or adjusted under 35 U.S.C. 154(b) by 279 days.

(21) Appl. No.: 12/746,141

(22) PCT Filed: Dec. 3, 2008

(86) PCT No.: PCT/GB2008/003996
§ 371 (c)(1),
(2), (4) Date: Sep. 8, 2010

(87) PCT Pub. No.: WO2009/071886
PCT Pub. Date: Jun. 11, 2009

(65) Prior Publication Data
US 2010/0323966 A1 Dec. 23, 2010

(30) Foreign Application Priority Data
Dec. 4, 2007 (GB) .................................. 0723712.6

(51) Int. Cl.
*A61K 38/10* (2006.01)
*A61K 38/37* (2006.01)

(52) U.S. Cl.
USPC .......... 514/21.5; 530/326; 530/383; 514/14.1

(58) Field of Classification Search
None
See application file for complete search history.

(56) References Cited

FOREIGN PATENT DOCUMENTS

| WO | WO 90/15615 | 12/1990 |
|---|---|---|
| WO | WO 02/16410 | 2/2002 |
| WO | WO 02/060917 | 8/2002 |
| WO | WO-02/060917 | * 8/2002 |
| WO | WO 02/098454 | 12/2002 |
| WO | WO 03/087161 | 10/2003 |
| WO | WO-03/087161 | * 10/2003 |
| WO | 2006/003183 A1 | 1/2006 |

OTHER PUBLICATIONS

Sugihara 2000, Nagoya J. Med. Sci., 63, 25-39.*
Jones, 2005, Journal of Thrombosis and Haemostasis, 3, 991-1000.*
Jones, et al., "Identification and Removal of a Promiscuous CD4+ T Cell Epitope from the C1 Domain of Factor VIII", Journal of Thrombosis and Haemostasis, 3, pp. 991-1000, 2005.
Sugihara, et al., "Identification of Plasma Antibody Epitopes and Gene Abnormalities in Japanese Hemophilia A Patients . . . ", Nagoya J. Med. Sci., 63, pp. 25-39, 2000.
Suchitra S. Acharya and Donna M. DiMichele—Management of Factor VIII Inhibitors—Best Practice & Research Clinical Haematology—Mar. 2006—pp. 51-66—vol. 19—Issue 1—USA.
Cezmi A. Akdis et al.—Role of Interleukin 10 in Specific Immunotherapy—The Journal of Clinical Investigation—Jul. 1998—pp. 98-106—vol. 102—No. 1—USA.
Marina Algiman et al.—Natural Antibodies to Factor VIII (Anti-Hemophilic Factor) in Healthy Individuals—Proceedings of the National Academy of Sciences of the United States of America—May 1992—pp. 3795-3799—vol. 89—USA.
Stephen M. Anderton and David C. Wraith—Hierarchy in the Ability of T Cell Epitopes to Induce Peripheral Tolerance to Antigens from Myelin—European Journal of Immunology—1998—pp. 1251-1261—vol. 28—Great.
Stephen M. Anderton et al.—Mechanisms of Central and Peripehral T-Cell Tolerance: Lessons from Experimental Models of Multiple Sclerosis—Immunological Reviews—1999—pp. 123-137—vol. 169—Denmark.
Christoph Burkhart et al.—Peptide-Induced T Cell Regulation of Experimental Autoimmune Encephalomyelitis: A Role for IL-10—International Immunology—1999—pp. 1625-1634—vol. 11—Great Britain.
Paul J. Fairchild et al.—The Nature of Cryptic Epitopes within the Self-Antigen Myelin Basic Protein—International Immunology—1996—pp. 1035-1043—vol. 8—No. 7—Great Britain.
Jane Gitschier et al.—Characterization of the Human Factor VIII Gene—Nature—Nov. 22, 1984—pp. 326-330—vol. 312—Great Britain.
David C. Horwell—The 'Peptoid' Approach to the Design of Non-Peptide, Small Molecule Agonists and Antagonists of Neuropeptides—Trends Biotechnology—Tibtech—Apr. 1995—pp. 132-134—vol. 13—No. 4—France.
George W. Liu and David C. Wraith—Affinity for Class II MHC Determines the Extent to which Soluble Peptides Tolerize Autoreactive T Cells in Naive and Primed Adult Mice—Implications for Autoimmunity—International Immunology—1995—pp. 1255-1263—vol. 7—No. 8—Great Britain.
Barbara Metzler and David C. Wraith—Inhibition of Experimental Autoimmune Encephalomyelitis by Inhalation but not Oral Administration of the Encephalitogenic Peptide: Influence of MHC Binding Affinity—International Immunology—1993—pp. 1159-1165—vol. 5—No. 9—Great Britain.
Alexandre Moreau et al.—Antibodies to the FVIII Light Chain that Neutralize FVIII Procoagulant Activity are Present in Plasma of Nonresponder Patients with Severe Hemophilia A and in Normal Polyclonal Human IgG—Blood—Jun. 1, 2000—pp. 3435-3441—vol. 95—No. 11—USA.
Ulrich Muller et al.—Successful Immunotherapy with T-Cell Epitope Peptides of Bee Venom Phospholipase A2 Induces Specific T-Cell Anergy in Patients Allergic to Bee Venom—The Journal of Allergy and Clinical Immunology—Jun. 1998—pp. 747-754—vol. 101.
Karen Nelson et al.—T-T Hybridoma Product Specifically Suppresses Tumor Immunity—Proceedings of the National Academy of Sciences of the United States of America—May 1980—pp. 2866-2870—vol. 77—No. 5—USA.

(Continued)

*Primary Examiner* — Satyanarayana R Gudibande
(74) *Attorney, Agent, or Firm* — Morgan, Lewis & Bockius LLP

(57) ABSTRACT

The present invention provides a peptide comprising a core residue sequence derivable from human FVIII which peptide is capable of binding to an MHC class II molecule without further antigen processing. The present invention also relates to the use of such peptides for the prevention or suppression of inhibitor antibody formation in haemophilia A and/or acquired haemophilia.

8 Claims, 14 Drawing Sheets

OTHER PUBLICATIONS

M.T. Reding—Immunological Aspects of Inhibitor Development—Haemophilia—2006—pp. 36-36—vol. 12 (Supplement 6)—USA.

Jacques Y. Roberge et al.—A Strategy for a Convergent Synthesis of N-Linked Glycopeptides on a Solid Support—Science—Jul. 14, 1995—pp. 202-204—vol. 269—USA.

Reyna J. Simon et al.—Peptoids: A Modular Approach to Drug Discovery—Proceedings of the National Academy of Sciences of the United States of America—Oct. 1992—pp. 9367-9371—vol. 89—USA.

Kelly L. Summers et al.—Phenotypic Characterization of Five Dendritic Cell Subsets in Human Tonsils—American Journal of Pathology—Jul. 2001—vol. 159—No. 1—USA.

William W. Wood et al.—Expression of Active Human Factor VIII from Recombinant DNA Clones—Nature—Nov. 22, 1984—pp. 330-337—vol. 312—Great Britain.

D. DiMichele—Immune Tolerance Therapy for Factor VIII Inhibitors: Moving from Empiricism to an Evidence-Based Approach—Journal of Thrombosis and Haemostasis—2007—pp. 143-150—vol. 5—Supplement 1—USA.

Charles Hay et al.—Current and Future Approaches to Inhibitor Management and Aversion—Seminars in Thrombosis and Hemostasis—2006—pp. 15-21—vol. 32—Supplement 2—USA.

* cited by examiner

FIG. 5

FVIII-/- clones specific for DNIMV

- F-M42 fresh
- F-M42 fix
- F-M58 fresh
- F-M58 fix
- F-M66 fresh
- F-M66 fix
- F-M76 fresh
- F-M76 fix Y-axis: IL-2 (pg/ml), 0 to 3000
X-axis: Mgar, Mgar+FVIII, Mgar+DNIMV

FVIII-/- clones specific for PRCLT

- F-M23 fresh
- F-M23 fix
- F-M24 fresh
- F-M24 fix
- F-M81 fresh
- F-M81 fix

Y-axis: IL-2 (pg/ml), 0 to 2000
X-axis: Mgar, Mgar+FVIII, Mgar+DNIMV

FIG. 7a

Mean IL-2 production for overlapping DNIMV peptides (8 clones)

FIG. 7b

Mean IL-2 production for overlapping PRCLT peptides (4 clones)

Mean IL-2 production for overlapping peptides
PPIIA, DTLLI, SLYIS and RYLRI

FVIII PEPTIDES AND THEIR USE IN TOLERISING HAEMOPHILIACS

RELATED APPLICATIONS

The present application is a U.S. National Phase Application of International Application No. PCT/GB2008/003996 (filed Dec. 3, 2008) which claims priority to Great Britian Patent Application No. 0723712.6 (filed Dec. 4, 2007) which are hereby incorporated by reference in their entirety.

SEQUENCE LISTING SUBMISSION VIA EFS-WEB

A computer readable text file, entitled "067024-5011-SeqListing.txt," created on or about Jun. 2, 2010 with a file size of about 42 kb contains the sequence listing for this application and is hereby incorporated by reference in its entirety.

FIELD OF THE INVENTION

The present invention relates to a peptide. In particular, it relates to peptides derivable from factor VIII (FVIII). The peptides can be used to reduce or prevent factor VIII inhibitor antibody formation, for example in haemophilia A treatment and acquired haemophilia.

BACKGROUND TO THE INVENTION

Haemophilia

Haemophilia belongs to a group of inheritable blood disorders that includes haemophilia A, haemophilia B (Christmas disease) and Von Willebrand's disease.

In haemophilia, the blood's ability to clot is severely reduced because an essential clotting factor is partly or completely missing, resulting in increased bleeding time. Haemophilia A is a deficiency of the clotting factor VIII, whereas Haemophilia B is a deficiency of clotting factor IX. In both diseases, the faulty gene is found on the X chromosome, so the conditions are X-linked. Haemophilia A is five times more common than haemophilia B.

Haemophilia is a lifelong inherited genetic condition, which affects females as carriers and males who inherit the condition. About a third of new diagnoses are where there is no previous family history. It appears world-wide and occurs in all racial groups. About 6,000 people are affected with haemophilia in the UK.

Haemophiliacs bleed for a prolonged period following injury. External injuries such as cuts and grazes do not usually pose serious problems: it is often possible to stop bleeding by applying a degree of pressure and covering the affected area (e.g with a plaster).

The main problem is internal bleeding into joints, muscles and soft tissues, which can occur spontaneously. Internal bleeding, such are haemorrhages into the brain, is very difficult to manage and can be fatal. Repeated bleeding in the joints causes acute pain and can cause arthritis and/or long-term joint damage leading to disability.

Treatment for haemophilia is usually by replacement of the missing clotting factor. In mild or moderate haemophilia injections may be given at the time a bleed occurs (on-demand therapy). However, in severe haemophilia regular prophylactic injections are given to help the blood to clot and minimise the likelihood of long term joint damage.

A potentially serious complication of coagulation factor replacement therapy for haemophilia A is the development of antibodies that neutralise the procoagulant function of factor VIII. Factor VIII inhibitors occur in approximately 25% of those with severe haemophilia A. Since patients with congenital haemophilia A can be genetically deficient in FVIII, the synthesis of inhibitors is an alloimmune response to the foreign protein administered to prevent or treat bleeding episodes.

CD4+ T cells play a central role in the immune response to FVIII. After being taken up by antigen-presenting cells (APCs), FVIII undergoes proteolytic degradation into peptide fragments (Reding et al (2006) Haemophilia 12(supp 6) 30-36). These peptides are then presented on the surface of the APC in association with MHC class II molecules. This complex is then recognised by the T cell receptor of a CD4+ cell specific for FVIII. In the presence of the appropriate costimulatory signals, this recognition ultimately causes the CD4+ cell to direct the synthesis of antibodies by B cells.

The incidence of inhibitor formation initially increases with the number of factor VIII treatments, but appears to plateau after 50-100 exposure days. Inhibitor formation is much more common in severe haemophilia than in moderate or mild disease and some molecular defects, most clearly large deletions and nonsense mutations in the factor VIII light chain, appear to predispose to inhibitor formation. Parameters such as the concentration, type (purified or recombinant) of replacement factor, and treatment history may also affect the likelihood of antibody production.

The management of haemophilia patients with inhibitors is an ongoing challenge. Immune tolerance induction (ITI) using a desensitization technique is successful in some patients with alloantibodies against factor VIII. This therapeutic approach requires ongoing exposure to factor replacement therapy, so is a long-term strategy.

Although ITI can be successful, a significant proportion (about 30%) of patients fail to respond to ITI. Patients with high inhibitor titres are much less likely to respond to treatment. Another significant contributing factor is age at the start of commencing ITI, with greatly decreased success rates when the patient is older than 20 (Hay et al (2005) Seminars in Thrombosis and Hemostasis 32:15-21)

When ITI therapy is unsuccessful, the inhibitor generally persists for life, and because such patients are usually high-responders, it is necessary to treat episodes of bleeding with FVIII bypassing products, such as activated prothombin complex concentrates (FEIBA™), and recombinant-activated FVII. However, the use of such agents is associated with adverse events such as disseminated intravascular coagulation, acute myocardial infarction, pulmonary embolus and thromboses (Acharya and DiMichele (2006) Best Practice & Research Clinical Haematology 19:51-66).

Immunosuppressive therapy is sometimes used for patients who fail to response to ITI. Treatment includes administration of immunosuppressive drugs such as cyclophosphamide, prednisone, azathioprine and cyclosporine which non-specifically target the immune system. These treatments can have side-effects associated with general immunosuppression.

There is renewed interest on selective B cell depletion using Rituximab™, a humanised monoclonal antibody to B cell CD20 antigen. However, infusion reactions, serum sickness and opportunistic infections have occurred in some children treated with this drug (DiMichele (2007) J Thromb Haemost 5:143-50).

Acquired Haemophilia

Acquired haemophilia is a rare autoimmune condition which affects between 1 and 4 people in every million. In this condition, subjects who are not born with haemophilia develop antibodies against one of the clotting factors such as factor VIII. It is thought that pregnancy and autoimmune diseases such as rheumatoid arthritis and cancer may increase the risk of developing acquired haemophilia. Although there are differences in the underlying immune mechanisms leading to their production, the clinical manifestations of FVIII inhibitors produced in response to coagulation factor replacement therapy and those produced in acquired haemophilia are similar.

Acquired haemophiliac patients have a mortality rate that approaches 25%, partly because of the association of acquired inhibitors with severe bleeding complications. The therapy of acquired autoantibody inhibitors is based primarily on the need to control or prevent acute hemorrhagic complications, which frequently are life and limb threatening and secondarily to eradicate the autoantibody to restore normal coagulation.

Some bleeds associated with low titre autoantibody inhibitors (<5 Bethesda Units) may be treated effectively with FVIII concentrates administered at high doses. Porcine FVIII concentrate was formerly considered a critical first-line therapy for acquired hemophilia-related bleeding since it was the only replacement therapy that provided an opportunity to actually measure post-infusion FVIII coagulation activity levels in the laboratory. The product was removed from the marketplace in 2004 because of contamination of the porcine plasma pools by porcine parvovirus. Now, "bypassing" agents are most commonly used, but potential risks of thrombogenicity exist and there is only about 80% efficacy for each product. Plasma exchange via plasmapheresis and extracorporeal immunoadsorption may be necessary to temporarily reduce the inhibitor titer enough for bypassing agents or FVIII replacement to provide adequate hemostasis.

Eradication of autoantibody inhibitors depends on immunosuppressive measures, such as: (1) administration of corticosteroids with 30%-50% efficacy in 3-6 weeks; (2) use of cytotoxic and myelosuppressive chemotherapeutic agents, e.g., cyclophosphamide, cyclosporine, 2-chlorodeoxyadenosine; (3) immunomodulation with intravenous immunoglobulin; and (4) selective B-lymphocyte depletion with rituximab. Rituximab™ responders may require concurrent use of steroids and relapses may respond to retreatment.

Thus, all currently available methods for reducing alloantibody production associated with haemophilia A treatment, and autoantibody production in acquired haemophilia, have shortcomings. There is therefore a need for improved methods to address the issue of anti-FVIII antibodies in haemophilia A and acquired haemophilia.

The present inventors have found that it is possible to prevent FVIII inhibitor antibody formation by pre-tolerising the patient with FVIII-derived peptides.

SUMMARY OF ASPECTS OF THE INVENTION

The present invention, therefore, relates to a peptide derivable from FVIII which is capable of inducing or restoring tolerance to FVIII.

The present inventors have identified a number of immunodominant regions of FVIII that are predicted to give rise to HLA-DR2 binding peptides (Table 1). Of these peptides, regions 545-559 and 1788-1803 of factor VIII are considered to represent the immunodominant T-cell epitope regions in the HLA-DR2 restricted T-cell response to human factor VIII. Treatment of mice with these peptides has been shown to lead to a substantial suppression of the immune response to factor VIII.

In a first aspect, the present invention provides a peptide comprising one of the following core residue sequences:

| | |
|---|---|
| LYISQFIIM | (SEQ ID NO: 2) |
| FIIMYSLDG | (SEQ ID NO: 3) |
| IARYIRLHP | (SEQ ID NO: 4) |
| LIIFKNQAS | (SEQ ID NO: 5) |
| LTRYYSSFV | (SEQ ID NO: 6) |
| MVTFRNQAS | (SEQ ID NO: 7) |
| LRIHPQSWV | (SEQ ID NO: 8) | which peptide is capable of binding to an MHC class II molecule without further antigen processing and being recognised by a factor VIII specific T cell.

The peptide may, for example, have the sequence PRCLTRYYSSFVNME (SEQ ID NO:9) or DNIMVTFRNQASRPY (SEQ ID NO:10).

In a second aspect, the present invention provides a composition, such as a pharmaceutical composition comprising a peptide of the first aspect of the invention. The composition may comprise a plurality of such peptides. In particular, the composition may comprise the following peptides: PRCLTRYYSSFVNME (SEQ ID NO:9) and DNIMVTFRNQASRPY (SEQ ID NO:10).

The composition may be in the form of a kit, in which the plurality of peptides are provided separately for separate, subsequent, sequential or simultaneous administration.

The peptide or a composition of the invention may be for use in suppressing, reducing, or preventing the development of factor VIII inhibitor antibodies.

The present invention also provides the use of such a peptide or composition in the manufacture of a medicament to suppress, reduce or prevent the development of factor VIII inhibitor antibodies.

The present invention also provides a method for suppressing, preventing or reducing the development of Factor VIII inhibitor antibodies in a subject, which comprises the step of administration of such a peptide or composition to the subject.

The subject may be deficient in FVIII. In particular the subject may have haemophilia A, and may be, or be about to, undergo factor VIII replacement therapy.

Alternatively the subject may have, or be at risk from contracting, acquired haemophilia.

Factor VIII inhibitors are found more frequently in individuals expressing HLA-DR2. The subject treated by the method of the invention may therefore be HLA-DR2 positive.

DESCRIPTION OF THE FIGURES

FIG. 5: FVIII−/− clones specific for a) DNIMV (SEQ ID NO:72) and b) PRCLT (SEQ ID NO:70)

Figure 1:
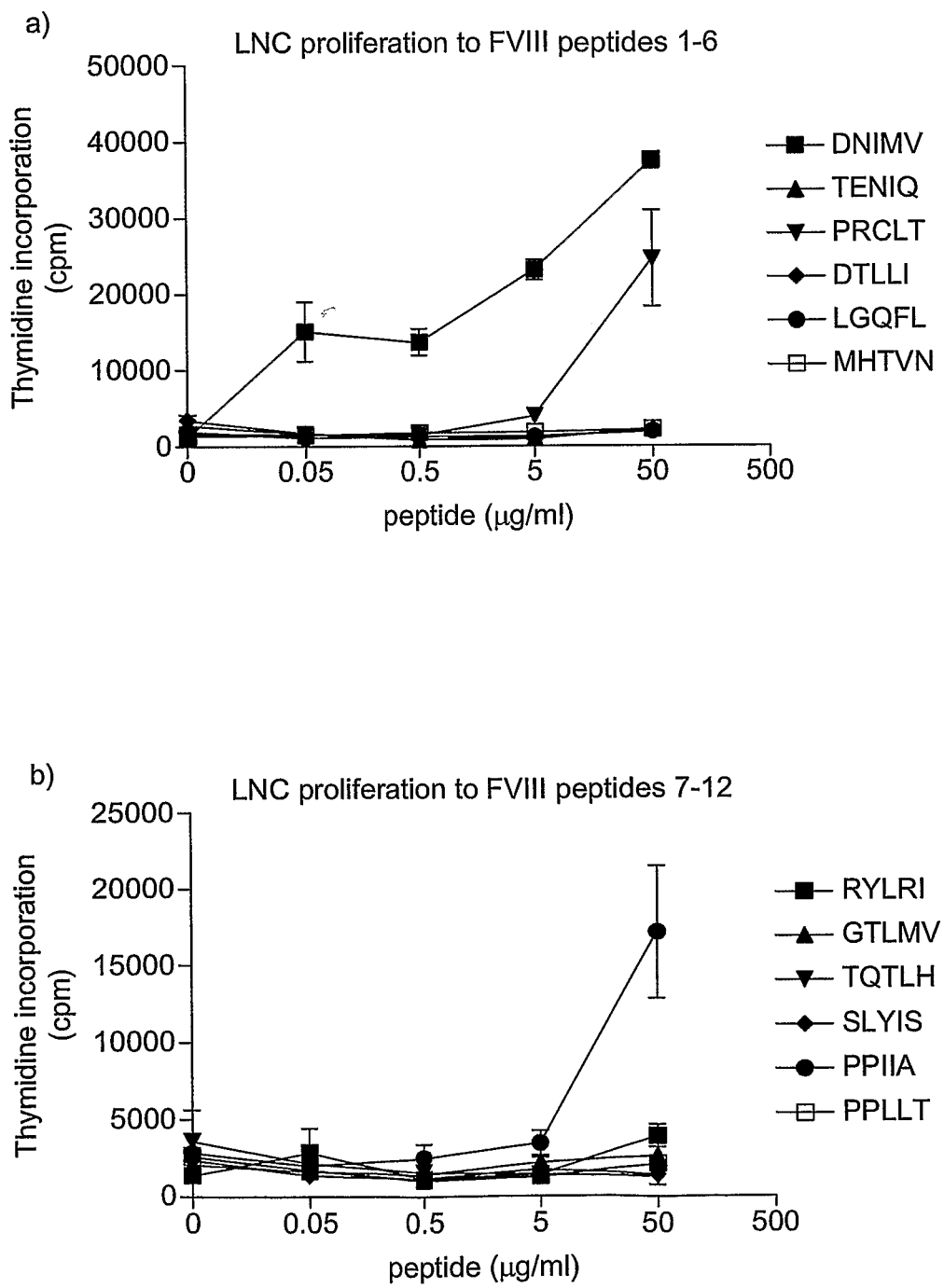
FIG. 1: Recall responses for lymph node cells (LNC) from FVIII+DR2+ mice primed with rhFVIII/CFA
 a) LNC proliferation to FVIII peptides 1-6
 b) LNC proliferation to FVIII peptides 7-12
 c) LNC proliferation to FVIII peptides 1, 3 and 11
Figure 1:
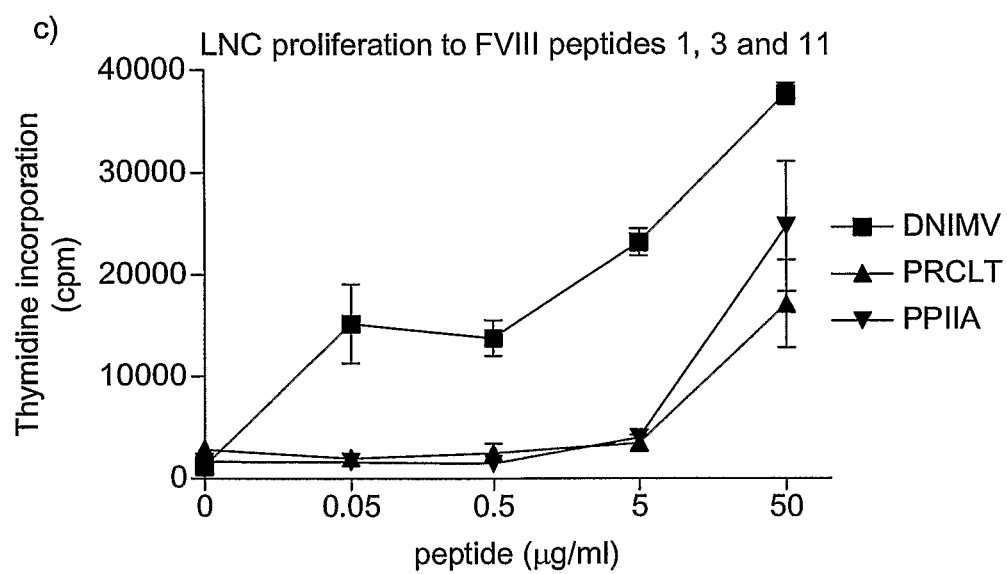

```
LYISQFIIM       (SEQ ID NO: 2)
FIIMYSLDG       (SEQ ID NO: 3)
IARYIRLHP       (SEQ ID NO: 4)
LIIFKNQAS       (SEQ ID NO: 5)
LTRYYSSFV       (SEQ ID NO: 6)
MVTFRNQAS       (SEQ ID NO: 7)
LRIHPQSWV       (SEQ ID NO: 8).
```

For example, the peptides may comprise one of the following core residue sequences:

```
IARYIRLHP       (SEQ ID NO: 4)
LTRYYSSFV       (SEQ ID NO: 6)
MVTFRNQAS       (SEQ ID NO: 7)
LRIHPQSWV       (SEQ ID NO: 8).
```

In particular, the peptides may comprise one of the following core residue sequences:

```
LTRYYSSFV       (SEQ ID NO: 6)
MVTFRNQAS       (SEQ ID NO: 7).
```

The peptide may comprise one of the core residue sequences, together with additional flanking sequences at the N and/or C terminal end, provided that the resulting peptide is capable of binding to an MHC class II molecule without further antigen processing.

The flanking N and/or C terminal sequences may be derivable from the sequences flanking the core residue sequences in human FVIII.

For example, the peptide may be selected from the following group:

```
SLYISQFIIMYSLDG   (SEQ ID NO: 11)
PPIIARYIRLHPTHY   (SEQ ID NO: 12)
DTLLIIFKNQASRPY   (SEQ ID NO: 13)
PRCLTRYYSSFVNME   (SEQ ID NO: 9)
DNIMVTFRNQASRPY   (SEQ ID NO: 10)
RYLRIHPQSWVHQIA   (SEQ ID NO: 14).
```

Some FVIII-derived peptides are already known to be antigen processing-independent epitopes (for example PRCLTRYYSSFVNME (SEQ ID NO:9) and DNIMVTFRNQASRPY (SEQ ID NO:10)). In addition to these peptides, there may be others which share the same core residue sequence, but which differ by one or more flanking residues.

In order to test this, a panel of overlapping peptides may be produced. Typically, a cluster of peptides within the set are be capable of generating an immune response, because they contain the minimal epitope. Of these peptides, one can investigate whether the peptide also behaves as an antigen processing-independent epitope, by investigating the capacity of the peptide to bind MHC class II and stimulate the appropriate T cell in an antigen processing free presentation system.

The peptides shown in the following table may be tested for their ability to act as antigen processing-independent epitopes:

```
SLYISQFIIMYSLDG   (SEQ ID NO: 11)
LYISQFIIMMYSLDGK  (SEQ ID NO: 15)
RQKFSSLYISQFIIM   (SEQ ID NO: 16)
QKFSSLYISQFIIMY   (SEQ ID NO: 17)
KFSSLYISQFIIMYS   (SEQ ID NO: 18)
FSSLYISQFIIMYSL   (SEQ ID NO: 19)
SSLYISQFIIMYSLD   (SEQ ID NO: 20)
YISQFIIMYSLDGKK   (SEQ ID NO: 21)
ISQFIIMYSLDGKKW   (SEQ ID NO: 22)
SQFIIMYSLDGKKWQ   (SEQ ID NO: 23)
QFIIMYSLDGKKWQT   (SEQ ID NO: 24)
FIIMYSLDGKKWQTY   (SEQ ID NO: 25)
IARYIRLHPTHYSIR   (SEQ ID NO: 26)
IIARYIRLHPTHYSI   (SEQ ID NO: 27)
PIIARYIRLHPTHYS   (SEQ ID NO: 28)
PPIIARYIRLHPTHY   (SEQ ID NO: 12)
NPPIIARYIRLHPTH   (SEQ ID NO: 29)
FNPPIIARYIRLHPT   (SEQ ID NO: 30)
IFNPPIIARYIRLHP   (SEQ ID NO: 31)
LIIFKNQASRPYNIY   (SEQ ID NO: 32)
LLIIFKNQASRPYNI   (SEQ ID NO: 33)
TLLIIFKNQASRPYN   (SEQ ID NO: 34)
DTLLIIFKNQASRPY   (SEQ ID NO: 13)
GDTLLLIIFKNQASRP  (SEQ ID NO: 35)
VGDTLLLIIFKNQASR  (SEQ ID NO: 36)
EVGDTLLLIIFKNQAS  (SEQ ID NO: 37)
KSDPRCLTRYYSSFV   (SEQ ID NO: 38)
SDPRCLTRYYSSFVN   (SEQ ID NO: 39)
DPRCLTRYYSSFVNM   (SEQ ID NO: 40)
PRCLTRYYSSFVNME   (SEQ ID NO: 9)
RCLTRYYSSFVNMER   (SEQ ID NO: 41)
CLTRYYSSFVNMERD   (SEQ ID NO: 42)
LTRYYSSFVNMERDL   (SEQ ID NO: 43)
EVEDNIMVTFRNQAS   (SEQ ID NO: 44)
VEDNIMVTFRNQASR   (SEQ ID NO: 45)
EDNIMVTFRNQASRP   (SEQ ID NO: 46)
DNIMVTFRNQASRPY   (SEQ ID NO: 10)
```

-continued

| | |
|---|---|
| NIMVTFRNQASRPYS | (SEQ ID NO: 47) |
| IMVTFRNQASRPYSF | (SEQ ID NO: 48) |
| MVTFRNQASRPYSFY | (SEQ ID NO: 49) |
| LRIHPQSWVHQIALR | (SEQ ID NO: 50) |
| YLRIHPQSWVHQIAL | (SEQ ID NO: 51) |
| RYLRIHPQSWVHQIA | (SEQ ID NO: 14) |
| TRYLRIHPQSWVHQI | (SEQ ID NO: 52) |
| LTRYLRIHPQSWVHQ | (SEQ ID NO: 53) |
| LLTRYLRIHPQSWVH | (SEQ ID NO: 54) |
| PLLTRYLRIHPQSWV | (SEQ ID NO: 55) |

Also, it may be that peptides slightly longer or shorter than the 15-mer peptides given in the above tables act as antigen processing-independent epitopes and are capable of tolerising a subject to factor VIII. The peptide may, for example be between 10 and 25 amino acids, in particular between 12 and 18 amino acids in length.

APIPS

Various antigen processing independent presentation systems (APIPS) are known, including:

a) fixed APC (with or without antibodies to CD28);

b) Lipid membranes containing Class I or II MHC molecules (with or without antibodies to CD28); and c) purified natural or recombinant MHC in plate-bound form (with or without antibodies to CD28).

All of these systems are capable of presenting antigen in conjunction with an MHC molecule, but are incapable of processing antigen. In all these systems the processing function is either absent or disabled. This makes it possible to investigate whether a peptide can bind to an MHC class I or II molecule and be presented to a T cell without further antigen processing.

The use of fixed APC to investigate T cell responses is well known in the art, for example in studies to investigate the minimal epitope within a polypeptide, by measuring the response to truncated peptides (Fairchild et al (1996) Int. Immunol 8:1035-1043). APC may be fixed using, for example formaldehyde (usually paraformaldehyde) or glutaraldehyde.

Lipid membranes (which may be planar membranes or liposomes) may be prepared using artificial lipids or may be plasma membrane/microsomal fractions from APC.

In use, the APIPS may be applied to the wells of a tissue culture plate. Peptide antigens are then added and binding of the peptide to the MHC portion of the APIPS is detected by addition of selected T cell lines or clones. Activation of the T cell line or clone may be measured by any of the methods known in the art, for example via $^3$H-thymidine incorporation or cytokine secretion.

Factor VIII

The peptide of the invention may be derivable from factor VIII.

Factor VIII participates in the intrinsic pathway of blood coagulation; factor VIII is a cofactor for factor IXa which, in the presence of Ca+2 and phospholipids, converts factor X to the activated form Xa.

The factor VIII gene produces two alternatively spliced transcripts. Transcript variant 1 encodes a large glycoprotein, isoform a, which circulates in plasma and associates with von Willebrand factor in a noncovalent complex. This protein undergoes multiple cleavage events. Transcript variant 2 encodes a putative small protein, isoform b, which consists primarily of the phospholipid binding domain of factor VIIIc. This binding domain is essential for coagulant activity.

The complete 186,000 base-pair sequence of the human factor VIII gene was elucidated in the mid 1980s (Gitschier et al (1984) Nature 312 326-330). At the same time, DNA clones encoding the complete 2351 amino acid sequence were used to produce biologically active factor VIII in cultured mammalian cells (Wood et al (1984) Nature 312:330-337). The complete 2,351 amino acid sequence for human factor VIII is given in SEQ ID No. 1.

The peptide of the present invention may be derivable from factor VIII. The peptide may, for example, consist of a contiguous sequence of amino acids from the factor VIII sequence. The peptide may be obtainable or obtained from cleavage of the factor VIII sequence.

The peptide may have one or more mutations, such as additions, substitutions or deletions from the wild-type sequence, as long as the peptide retains the capacity to bind to the peptide-binding groove of an MHC molecule without further antigen processing, and be recognised by the relevant T cell. The peptide may, for example, have five, three, two or one mutation(s) over its length, when compared to the wild-type sequence.

Deliberate amino acid substitutions may be made on the basis of similarity in polarity, charge, solubility, hydrophobicity, hydrophilicity, and/or the amphipathic nature of the residues as long as the binding activity of the peptide is retained.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl- Phe*, L-Phe (4-amino)$^4$, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Tolerance

T cell epitopes play a central role in the adaptive immune response to any antigen, whether self or foreign. The central role played by T cell epitopes in hypersensitivity diseases (which include allergy, autoimmune diseases and transplant rejection) has been demonstrated through the use of experimental models. It is possible to induce inflammatory or allergic diseases by injection of synthetic peptides (based on the structure of T cell epitopes) in combination with adjuvant.

By contrast, it has been shown to be possible to induce immunological tolerance towards particular antigens by administration of peptide epitopes in soluble form. Administration of soluble peptide antigens has been demonstrated as an effective means of inhibiting disease in experimental autoimmune encephalomyelitis (EAE—a model for multiple sclerosis (MS)) (Metzler and Wraith (1993) Int. Immunol 5:1159-1165; Liu and Wraith (1995) Int. Immunol 7:1255-1263; Anderton and Wraith (1998) Eur. J. Immunol. 28:1251-1261); and experimental models of arthritis, diabetes, and uveoretinitis (reviewed in Anderton and Wraith (1998) as above). This has also been demonstrated as a means of treating an ongoing disease in EAE (Anderton and Wraith (1998) as above).

Tolerance is the failure to respond to an antigen. Tolerance to self antigens is an essential feature of the immune system, when this is lost, autoimmune disease can result. The adaptive immune system must maintain the capacity to respond to an enormous variety of infectious agents while avoiding autoimmune attack of the self antigens contained within its own tissues. This is controlled to a large extent by the sensitivity of immature T lymphocytes to apoptotic cell death in the thymus (central tolerance). However, not all self antigens are detected in the thymus, so death of self-reactive thymocytes remains incomplete. There are thus also mechanisms by which tolerance may be acquired by mature self-reactive T lymphocytes in the peripheral tissues (peripheral tolerance). A review of the mechanisms of central and peripheral tolerance is given in Anderton et al (1999) (*Immunological Reviews* 169:123-137).

In haemophilia A, patients have a defect in the factor VIII gene. This means that factor VIII is not recognised as a "self" antigen by the immune system. When factor VIII is administered during coagulation factor replacement therapy, therefore, an alloimmune response is generated to the foreign protein, leading to the production of FVIII inhibitor antibodies.

The peptides of the present invention are capable of inducing tolerance to factor VIII such that when FVIII is administered therapeutically, it does not induce an immune response and FVIII inhibitors do not develop.

Acquired haemophilia is an autoimmune disease in which tolerance to factor VIII breaks down. In this case, peptides of the present invention may be administered to reinstate tolerance to this self protein and curtail the pathogenic immune response.

Tolerance may result from or be characterised by the induction of anergy in at least a portion of CD4+ T cells. In order to activate a T cell, a peptide must associate with a "professional" APC capable of delivering two signals to T cells. The first signal (signal 1) is delivered by the MHC-peptide complex on the cell surface of the APC and is received by the T cell via the TCR. The second signal (signal 2) is delivered by costimulatory molecules on the surface of the APC, such as CD80 and CD86, and received by CD28 on the surface of the T cell. It is thought that when a T cell receives signal 1 in the absence of signal 2, it is not activated and, in fact, becomes anergic. Anergic T cells are refractory to subsequent antigenic challenge, and may be capable of suppressing other immune responses. Anergic T cells are thought to be involved in mediating T cell tolerance.

Without wishing to be bound by theory, the present inventors predict that peptides which require processing before they can be presented in conjunction with MHC molecules do not induce tolerance because they have to be handled by mature antigen presenting cells. Mature antigen presenting cells (such as macrophages, B cells and dendritic cells) are capable of antigen processing, but also of delivering both signals 1 and 2 to a T cell, leading to T cell activation. Antigen processing-independent epitopes, on the other hand, will be able to bind class II MHC on immature APC. Thus they will be presented to T cells without costimulation, leading to T cell anergy and tolerance.

Of course, antigen processing-independent epitopes are also capable of binding to MHC molecules at the cell surface of mature APC. However, the immune system contains a greater abundance of immature than mature APC (it has been suggested that less than 10% of dendritic cells are activated, Summers et al. (2001) Am. J. Pathol. 159: 285-295). The default position to an antigen processing-independent epitope will therefore be anergy/tolerance, rather than activation.

The induction of tolerance to FVIII can be monitored in vivo by looking for a reduction in the level of:

(i) FVIII inhibitory antibodies:
(ii) CD4+ T cells specific for FVIII
(iii) B cells capable of secreting FVIII inhibitory antibodies by techniques known in the art.

It has been shown that, when tolerance is induced by peptide administration, the capacity of antigen-specific CD4+ T cells to proliferate is reduced. Also, the production of IL-2, IFN-γ and IL-4 production by these cells is down-regulated, but production of IL-10 is increased. Neutralisation of IL-10 in mice in a state of peptide-induced tolerance has been shown to restore completely susceptibility to disease. It has been proposed that a population of regulatory cells persist in the tolerant state which produce IL-10 and mediate immune regulation (Burkhart et al (1999) Int. Immunol 11:1625-1634).

The induction of tolerance can therefore also be monitored by various techniques including:

(a) the induction of anergy in CD4+ T cells (which can be detected by subsequent challenge with FVIII in vitro);
(b) changes in the CD4+ T cell population, including
(i) reduction in proliferation;

(ii) down-regulation in the production of IL-2, IFN-γ and IL-4; and (iii) increase in the production of IL-10.

As used herein, the term "tolerogenic" means capable of inducing tolerance.

Composition

The present invention also relates to a composition, such as a pharmaceutical composition comprising a peptide according to the invention.

The peptide may comprise a plurality of peptides, for example, two, three, four, five or six peptides of the invention.

The peptides of the composition may each comprise a different minimal epitope. For example, the peptides may each comprise a minimal epitope from the peptides given in Table 1.

The composition may comprise the peptides PRCLTRYYSSFVNME (SEQ ID NO:9) and DNIMVTFRNQASRPY (SEQ ID NO:10).

The composition of the present invention may be for prophylactic or therapeutic use.

When administered for prophylactic use, the composition may reduce or prevent the generation of an immune response to FVIII. The level of immune response is less than would have been obtained in the patient had not been treated with the composition. The term "reduce" indicates that a partial reduction in immune response is observed, such as a 50%, 70%, 80% or 90% reduction in the response that would have been observed in the patient had not been treated with the composition (or in the response observed in an untreated patient over the same time-frame). The term "prevent" indicates that no appreciable immune response to FVIII is observed.

When administered for therapeutic use, the composition may suppress an already ongoing immune response to FVIII. The term "suppress" indicates a reduction in the level of an on-going immune response, compared to the level before peptide treatment, or the level which would have been observed at the same time point had the treatment not been given.

Treatment with the composition of the present invention may cause a reduction in levels of any or all of the following:

(i) FVIII inhibitory antibodies:

(ii) CD4+ T cells specific for FVIII (iii) B cells secreting FVIII inhibitory antibodies.

Detection of all these factors can be carried out by techniques known in the art, such as ELISA, FACS etc.

Treatment with the composition of the present invention may also or alternatively cause anergy in CD4+ T cells specific for FVIII. Anergy can be detected by for example subsequent challenge with FVIII in vitro.

It is important to bear in mind that not all immune responses to FVIII are pathogenic. Non-inhibitory anti-FVIII antibodies may be found in haemophilia patients without inhibitors (Moreau et al (2000) Blood 95:3435-41) and approximately 15% of healthy blood donors (Algiman et al (1992) 89:3795-9).

FVIII inhibitors may be detected by the Nijmegen modification of the clotting Bethesda assay, in which the ability of the patient's plasma to inactivate FVIII in normal plasma is tested. A Bethesda unit is defined as the amount of antibody that neutralizes 50% of plasma FVIII activity, and titres of 0.6 BU or greater suggest the presence of antibody.

Inhibitors are generally classified as low titre if the level is $<5$ BU and high titre if $>5$ BU.

The level of circulating FVIII inhibitory antibodies may be reduced to 90%, 75%, 50%, 20%, 10% 5% of the level of antibodies which would have been observed had the patient not received treatment.

The level of circulating FVIII inhibitory antibodies may be reduced to 5, 4, 3, 2, 1 or 0.5 BU.

The peptides and composition of the invention may increase the amount or proportion of therapeutically administered FVIII which is available to aid clotting in a patient. This is due to the reduction in FVIII inhibitors which may effectively remove a proportion of FVIII from exerting its therapeutic function. The peptide or composition of the invention may increase the amount of available FVIII by, for example, 10%, 25%, 50% 75% or 100%.

The peptides and composition of the invention may thus reduce the amount of FVIII which needs to be administered to aid clotting in a patient.

Formulation

The composition may by prepared as an injectable, either as liquid solution or suspension; solid form suitable for solution in, or suspension in, liquid prior to injection may also be prepared. The preparation may also be emulsified, or the peptides encapsulated in liposomes. The active ingredients may be mixed with excipients which are pharmaceutically acceptable and compatible with the active ingredient. Suitable excipients are, for example, water, saline (for example, phosphate-buffered saline), dextrose, glycerol, ethanol, or the like and combinations thereof.

In addition, if desired, the composition may contain minor amounts of auxiliary substances such as wetting or emulsifying agents and/or pH buffering agents. Buffering salts include phosphate, citrate, acetate. Hydrochloric acid and/or sodium hydryoxide may be used for pH adjustment. For stabilisation, disaccharides may be used such as sucrose or trehalose.

If the composition comprises a plurality of peptides, the relative ratio of the peptides may be approximately equal. Alternatively the relative ratios of each peptide may be altered, for example, to focus the tolerogenic response on a particular sub-set of autoreactive T-cells or if it is found that one peptide works better than the others in particular HLA types.

After formulation, the composition may be incorporated into a sterile container which is then sealed and stored at a low temperature, for example 4° C., or it may be freeze-dried.

Conveniently the composition is prepared as a lyophilized (freeze dried) powder. Lyophilisation permits long-term storage in a stabilised form. Lyophilisation procedures are well known in the art, see for example devicelink.com/ivdt/archive/97/01/006.html. Bulking agents are commonly used prior to freeze-drying, such as mannitol, dextran or glycine.

The composition may be administered in a convenient manner such as by the oral, intravenous (where water soluble), intramuscular, subcutaneous, sublingual, intranasal, intradermal or suppository routes or implanting (e.g. using slow release molecules).

The composition may advantageously be administered via intranasal, subcutaneous or intradermal routes.

The peptide and composition of the invention may be used to treat a human subject. The subject may have haemolphilia A, in particular severe haemophilia A. The subject may be genetically deficient in FVIII. The subject may have acquired haemophilia. The subject may have inhibitory anti-FVIII antibodies.

The subject may be undergoing or about to undergo coagulant replacement therapy with FVIII.

The subject may be undergoing or about to undergo gene therapy with the FVIII gene.

The subject may be an HLA-haplotype which is associated with a predisposition to develop inhibitory anti-FVIII alloantibodies or autoantibodies. The subject may express HLA- DR2. Methods for determining the HLA haplotype of an individual are known in the art.

Typically, a physician will determine the actual dosage which will be most suitable for an individual subject and it will vary with the age, weight and response of the particular patient.

In a preferred embodiment a "dose escalation" protocol may be followed, where a plurality of doses is given to the patient in ascending concentrations. Such an approach has been used, for example, for phospholipase A2 peptides in immunotherapeutic applications against bee venom allergy (Müller et al (1998) J. Allergy Clin Immunol 101:747-754 and Akdis et al (1998) J. Clin. Invest. 102:98-106).

Kits

Conveniently, if the composition comprises a plurality of peptides, they may be administered together, in the form of a mixed composition or cocktail. However, there may be circumstances in which it is preferable to provide the peptides separately in the form of a kit, for simultaneous, separate, sequential or combined administration.

The kit may also comprise mixing and/or administration means (for example a vapouriser for intranasal administration; or a syringe and needle for subcutaneous/intradermal dosing). The kit may also comprise instructions for use.

The pharmaceutical composition or kit of the invention may be used to treat and/or prevent a disease.

In particular, the composition/kit may be used to treat and/or prevent haemophilia A or acquired haemophilia.

Haemophilia A

Hemophilia A (classic hemophilia), is caused by the deficiency of Factor VIII.

Hemophilia A has an estimated incidence of 1 in 10,000 males, while hemophilia B is estimated to occur in one in 40,000 males. Approximately 1 woman in 5,000 is a carrier for hemophilia A, and 1 in 20,000 is a carrier of hemophilia B.

Hemophilia is typically divided into three classes: severe, moderate and mild, based on the level of clotting factor in the blood. In severe hemophilia, there is less than 1 percent of normal clotting factor. The degree of severity tends to be consistent from generation to generation.

Contrary to popular belief, minor cuts and wounds do not usually present a threat to hemophiliacs. Rather, the greatest danger comes from spontaneous bleeding that may occur in joints and muscles. This is most prone to occur during years of rapid growth, typically between the ages of 5 and 15 years.

Repeated spontaneous bleeding in joints may cause arthritis, and adjacent muscles become weakened. Pressure on nerves caused by the accumulation of blood may result in pain, numbness, and temporary inability to move the affected area.

Haemophilia A is usually diagnosed with a blood test to determine the effectiveness of clotting and to investigate whether the levels of clotting factors are abnormal.

The development of purified clotting factors in the 1970s, isolated from donated blood, significantly improved the long-term outlook for hemophiliacs. Mild to moderate haemophiliacs can use treatment with FVIII on an ad hoc basis, whereas severe haemophiliacs may require regular, indefinite treatment.

Previously, patients were given factor VIII concentrates pooled from thousands of plasma donations. This lead to significant problems of contamination with viral pathogens, particularly the human immunodeficiency virus and the hepatitis viruses.

Monoclonal antibody purification techniques, heat inactivation, and virucidal detergent treatments have rendered plasma-derived concentrates relatively safe.

Recombinant DNA technology has now provided a series of synthetic products, such as Recombinate™ and Kogenate™. Kogenate is made using baby hamster kidney cells expressing human factor VIII. The resulting factor is highly purified, eliminating any possibility of transmission of virus from plasma.

The peptide or composition of the present invention may be administered before and/or during factor VIII replacement therapy.

Hemophilia A is an ideal disease target for gene therapy since i) it is caused by a mutations in a single identified gene, ii) a slight increase in clotting factor levels in vivo can convert severe hemophilia into milder disease, and iii) current replacement therapies are considered suboptimal. Also, there is a wide range of safety if there is an "overshoot" of desired level of coagulation activity.

Unfortunately, to date the promise of gene therapy as a cure for haemophilia has not been realized, primarily because of difficulties in finding a gene delivery system which is sufficiently non-immunogenic to allow for long term expression of the clotting factor.

The peptides of the present invention would also be suitable for tolerising a subject prior to gene therapy with factor VIII and/or managing FVIII inhibitor formation in a patient following gene therapy.

Acquired Haemophilia

Acquired haemophilia is characterised by the presence of autoantibody inhibitors against FVIII in individuals with previously normal coagulation. It is a rare condition, with an estimated incidence of 1-3 per million population per year. The mortality rate associated with acquired autoantibody inhibitors approaches 25% versus the substantially lower risk of death in those with alloantibodies.

Compared to alloantibody inhibitor patients, acquired hemophilia is characterized by: (1) a more severe bleeding pattern; (2) higher incidence in older population; (3) occurrence in conjunction with identifiable underlying autoimmune diseases, lymphoproliferative or solid tumor malignancies, pregnancy, and use of certain antibiotics such as penicillin and sulfonamides in approximately 50% of cases; and (4) in vitro inhibitor activity that follow a type II pharmacokinetic pattern with incomplete neutralization of the targeted clotting factor activity by the autoantibody, typically resulting in residual factor VIII levels ranging between 2%-18% in patient plasma.

The peptide or composition of the present invention may be administered to a patient with acquired haemophilia, or to a patient believed to be at risk of developing acquired haemophilia due to, for example:

i) imminent treatment with, for example penicillin or a sulformamide
ii) progression of a tumour or other malignancy
iii) imminent or early pregnancy.

The invention will now be further described by way of Examples, which are meant to serve to assist one of ordinary skill in the art in carrying out the invention and are not intended in any way to limit the scope of the invention.

EXAMPLES

Example 1

Selection of HLA-DR2 Factor VIII Peptides

A series of FDVIII 15mer peptides were compared using three HLA-DR binding algorithms:
SYFPEITHI (syfpeithi.de/home.htm)
ProPred (imtech.res.in/raghava/propred/) and
and IEDB (immuneepitope.org/home.do).

Peptides were selected which were predicted to be HLA-DR2-binding by more than one of the programmes and flanking sequences were designed for the predicted core residues (table 1).

TABLE 1

| Peptide No | FVIII First AA | Sequence in single amino acid code | Also referred to herein as: |
|---|---|---|---|
| 1 | 2140 | GTLMVFFGNVDSSGI | GTLMV (SEQ ID NO: 62) |
| 2 | 0208 | TQTLHKFILLFAVFD | TQTLH (SEQ ID NO: 63) |
| 3 | 2114 | SLYISQFIIMYSLDG | SLYIS (SEQ ID NO: 64) |
| 4 | 2161 | PPIIARYIRLHPTHY | PPIIA (SEQ ID NO: 65) |
| 5 | 2318 | PPLLTRYLRIHPQSW | PPLLT (SEQ ID NO: 66) |
| 6 | 250 | MHTVNGYVNRSLPGL | MHTVN (SEQ ID NO: 67) |
| 7 | 322 | LGQFLLFCHISSHQH | LGQFL (SEQ ID NO: 68) |
| 8 | 478 | DTLLIIFKNQASRPY | DTLLI (SEQ ID NO: 69) |
| 9 | 545 | PRCLTRYYSSFVNME | PRCLT (SEQ ID NO: 70) |
| 10 | 607 | TENIQRFLPNPAGVQ | TENIQ (SEQ ID NO: 71) |
| 11 | 1788 | DNIMVTFRNQASRPY | DNIMV (SEQ ID NO: 72) |
| 12 | 2322 | RYLRIHPQSWVHQIA | RYLRI (SEQ ID NO: 73) |

Example 2

Investigating the Response of HLA-DR2 Restricted Cells from Factor VIII Immunised Mice to Peptides HLA-DR2 transgenic mice were immunised with human factor VIII in adjuvant. Draining lymph node cells were collected and restimulated in vitro with different concentrations of the 12 peptides from table 1. The results are shown in FIG. 1.

HLA-DR2 restricted cells from factor VIII immunised mice clearly respond strongly to peptide DNIMV (SEQ ID NO: 72) ($1^{st}$ amino acid 1788). There are also responses to peptides PRCLT (SEQ ID NO: 70) (545) and PPIIA (SEQ ID NO: 65) (2161).

Example 3

Investigating the Response of T Cells from HLA-DR2 Mice to Peptides

HLA-DR2 mice were first immunised with factor VIII in adjuvant. Spleen cells from immune mice were restimulated in vitro with factor VIII and the resulting lymphoblasts were fused with the BW5147 thymoma using polyethylene glycol.

Figure 2:
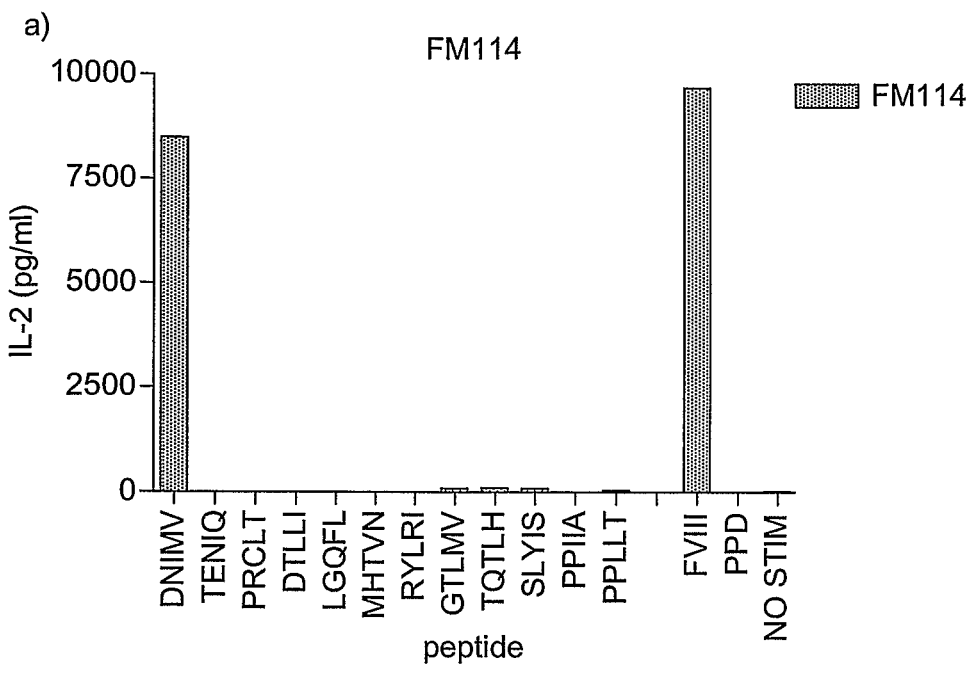
FIG. 2: Representative examples of FVIII+DR2+ T cell hybridoma clones specific for FVIII-derived peptides
Figure 2:
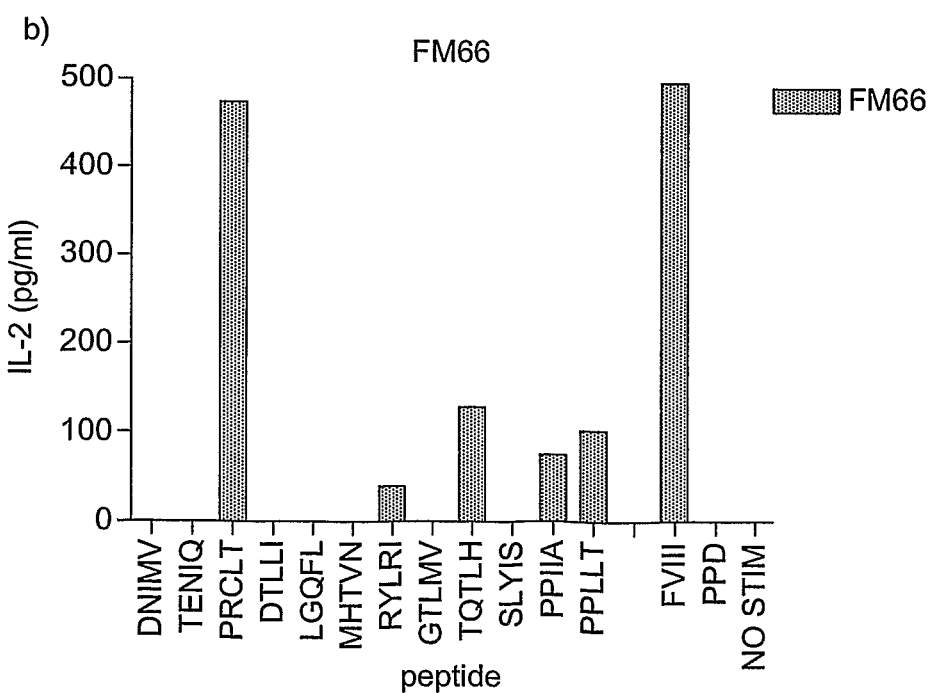

T-cell hybridomas were selected in HAT medium and the hybridomas cloned and tested for their response to factor VIII. The hybridomas were then screened for their response to the 12 predicted peptides. Of the 27 hybridomas screened, 11 responded to DNIMV (SEQ ID NO:72), 3 to PRCLT (SEQ ID NO:70) and 3 to PPIIA (SEQ ID NO:65), although the response to PPIIA (SEQ ID NO:65) was weaker and less specific. The response of two hybridomas specific for DNIMV (SEQ ID NO:72) and PRCLT (SEQ ID NO:70) is shown in FIG. 2.

Example 4

Investigating the Response of Lymph Node Cells from FVIII-DR2+ Mice to Peptides

HLA-DR2 transgenic mice were crossed with factor VIII deficient mice to create a model of haemophilia expressing the human HLA class II MHC molecule.

Figure 3:
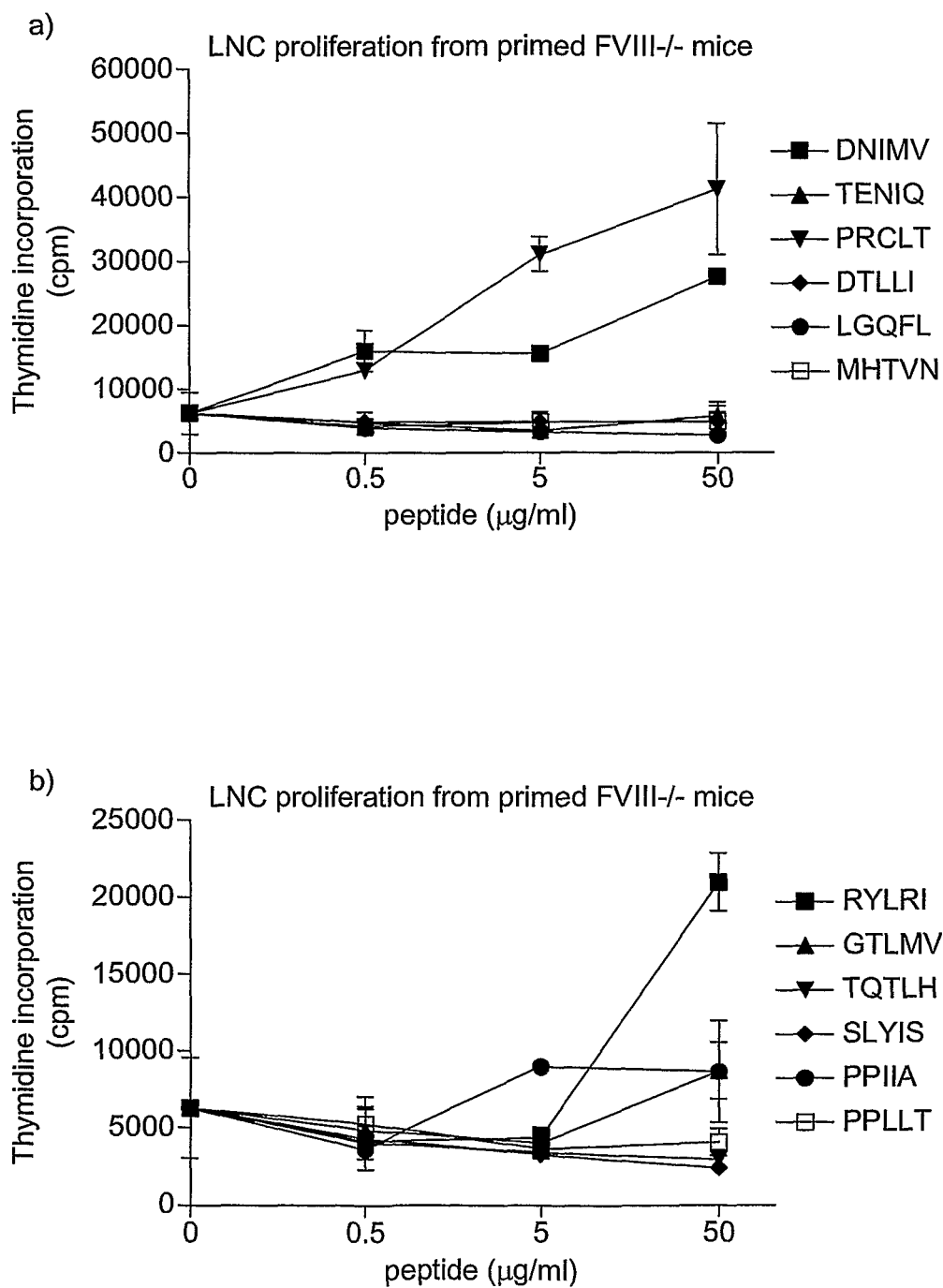
FIG. 3: Recall responses for LNC from FVIII-DR2+ mice primed with rhFVIII/CFA
Figure 3:
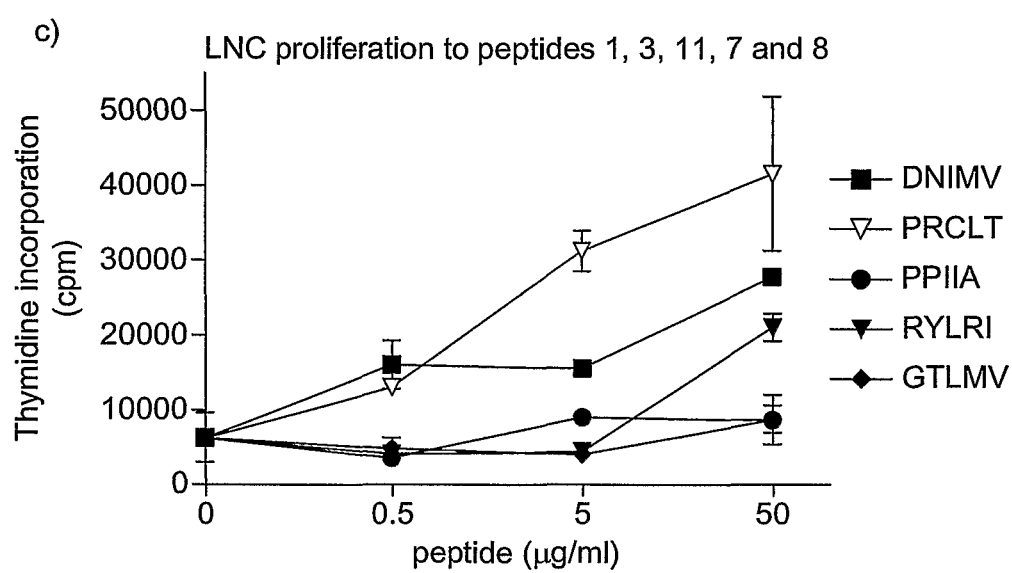

These FVIII-DR2+ animals were immunised with factor VIII in adjuvant. Draining lymph nodes were isolated and tested for their response to the peptide panel. As shown in FIG. 3, these cells responded well to PRCLT (SEQ ID NO:70) and DNIMV (SEQ ID NO:72). There was a weak response to GTLMV (SEQ ID NO:62) and significant response to RYLRI (SEQ ID NO:73).

Example 5

Investigating the Response of T Cells from HLA-DR2 Mice to Peptides

Figure 4:
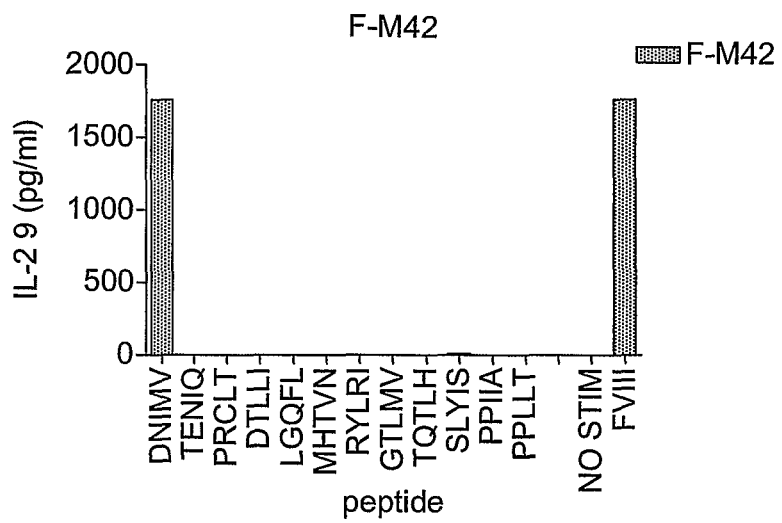
FIG. 4: Representative examples of FVIII-DR2+ T cell hybridoma clones specific for FVIII-derived peptides
Figure 4:
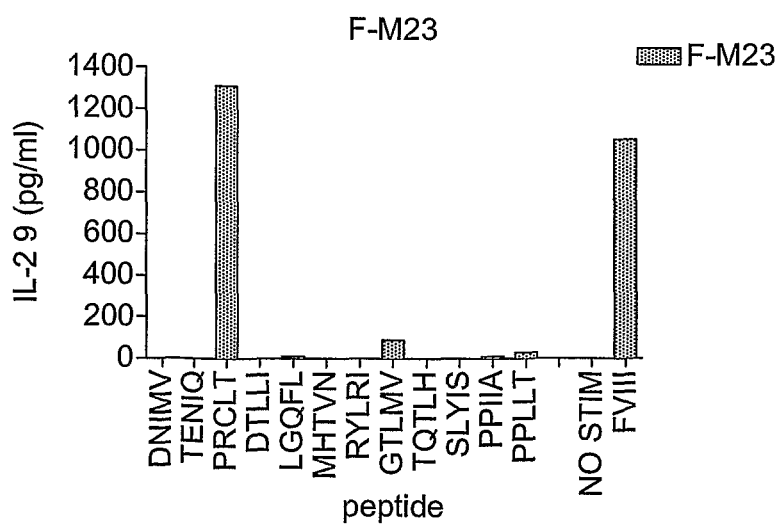
Figure 4:
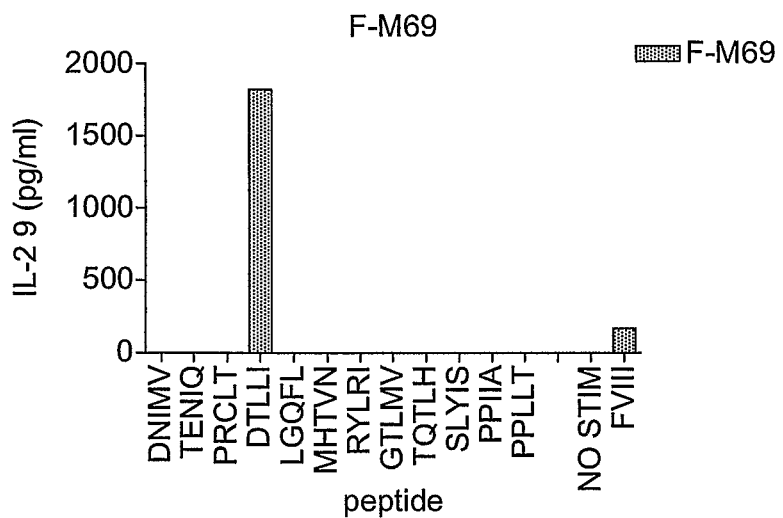
Figure 4:
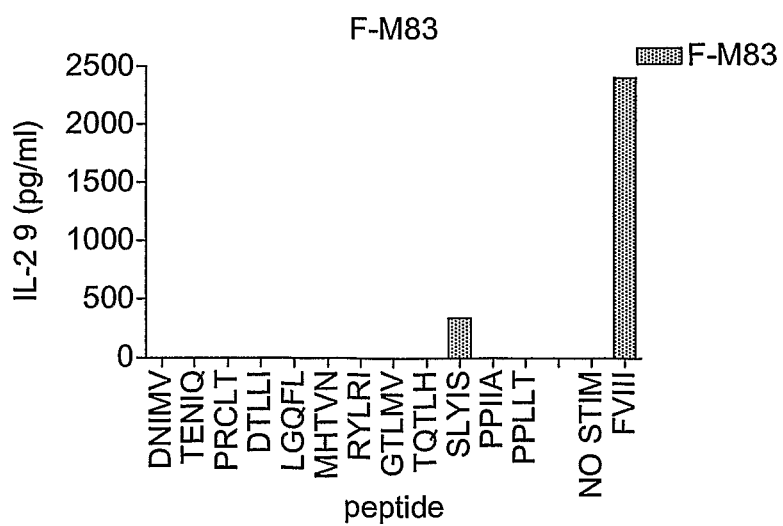

Factor VIII deficient mice expressing HLA-DR2 were immunised with factor VIII in adjuvant. Spleen cells from the immunised mice were restimulated in vitro with factor VIII and the resulting lymphoblasts were fused with BW5147, as described above. T-cell hybridomas were screened for their response to the 12 predicted peptides. Yet again, the majority of hybridomas responded to peptides DNIMV (SEQ ID NO:72) and PRCLT (SEQ ID NO:70). Of 19 hybridomas specific for factor VIII, 10 responded to DNIMV (SEQ ID NO:72), 6 to PRCLT (SEQ ID NO:70), 1 to PPIIA (SEQ ID NO:65), 1 to SLYIS (SEQ ID NO:64) and 1 to DTLLI (SEQ ID NO:69). Examples of responses by these hybridomas are shown in FIG. 4.

Based on these experiments it is clear that two peptides DNIMV (SEQ ID NO: 72) (first amino acid number 1788) and PRCLT (SEQ ID NO: 70) (first amino acid 545) constitute the immunodominant T-cell epitopes in the HLA-DR2 restricted T-cell response to human factor VIII.

Example 6

DNIMV (SEQ ID NO:72) and PRCLT (SEQ ID NO:70) Behave as Antigen Processing-Independent Epitopes In order to be an antigen processing-independent epitope, a peptide must be capable of binding to an MHC class I or II molecule without further antigen processing (i.e. trimming) and be presented to a T cell. In the present case, the capacity of peptides to be presented by fixed APC was investigated.

Mgar cells were either fresh or fixed with 1% paraformaldehyde. Clones were tested for antigenic specificity by culturing 100 µl of hybridoma cells with $5\times10^4$ Mgar cells in the presence and absence of 20 µg/ml rhFVIII or peptide epitopes overnight. Supernatants were then collected and assessed for IL-2 production by ELISA. The fact that rhFVIII must be presented by live Mgar cells demonstrates that the intact protein requires antigen processing to be presented. Peptides DNIMV (SEQ ID NO:72) and PRCLT (SEQ ID NO:70), on the other hand, are presented by both live and fixed Mgar cells indicating that these peptides function as antigen processing-independent epitopes (FIG. 5).

Example 7

Determination of the Range of Peptide Epitopes Capable of Functioning as Antigen Processing-Independent Epitopes The range of peptide epitopes capable of functioning as antigen processing-independent epitopes in the sequences surrounding DNIMV (SEQ ID NO:72), PRCLT (SEQ ID NO:70) and the other peptides was identified by preparing panels of overlapping peptides (shown on pages 36-37) and screening these using the T-cell hybridomas using the same method as Example 5 (FIG. 7).

Example 8

Figure 6:
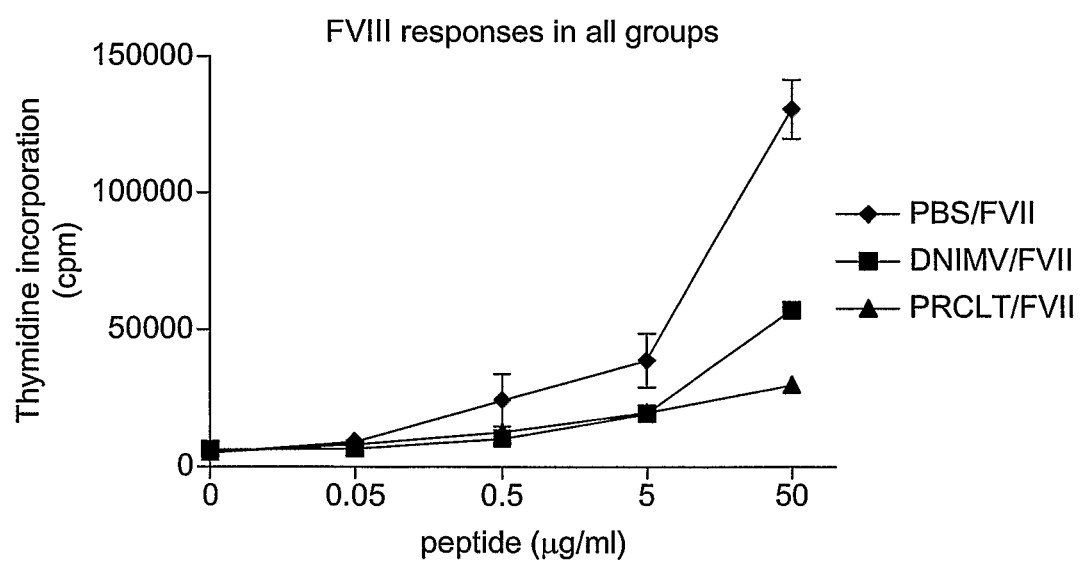
FIG. 6: Recall responses for LNC to FVIII for FVIII+ DR2+ mice treated 3×i.p. with peptide prior to priming with rhFVIII/CFA.
Figure 7C:
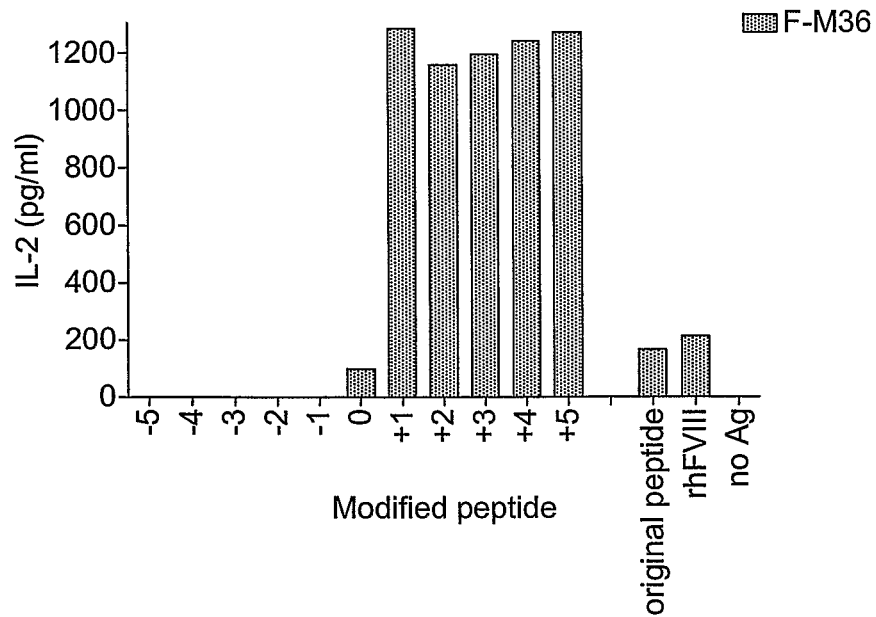
FIG. 7: Determination of the range of peptide epitopes capable of functions as antigen processing-independent epitopes using FVIII-DR2+ T cell hydridoma clones specific for FVIII-derived overlapping peptides. The original peptide is termed 0. One amino acid shift towards the N-terminal is −1, two amino acid shifts towards the N-terminal is −2 et Peptide Sequences The first aspect of the invention relates to a peptide comprising one of the following core residue sequences.
Figure 7C:
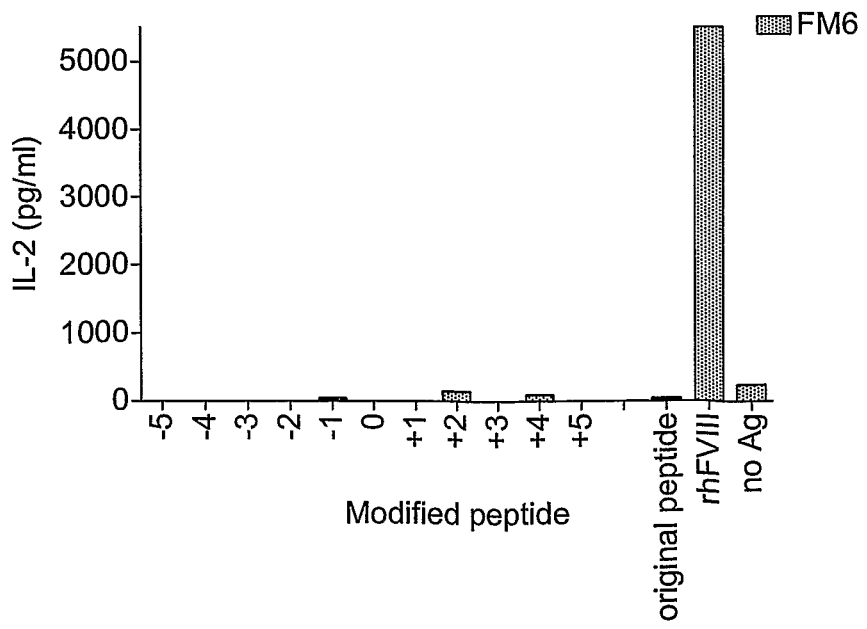
Figure 7C:
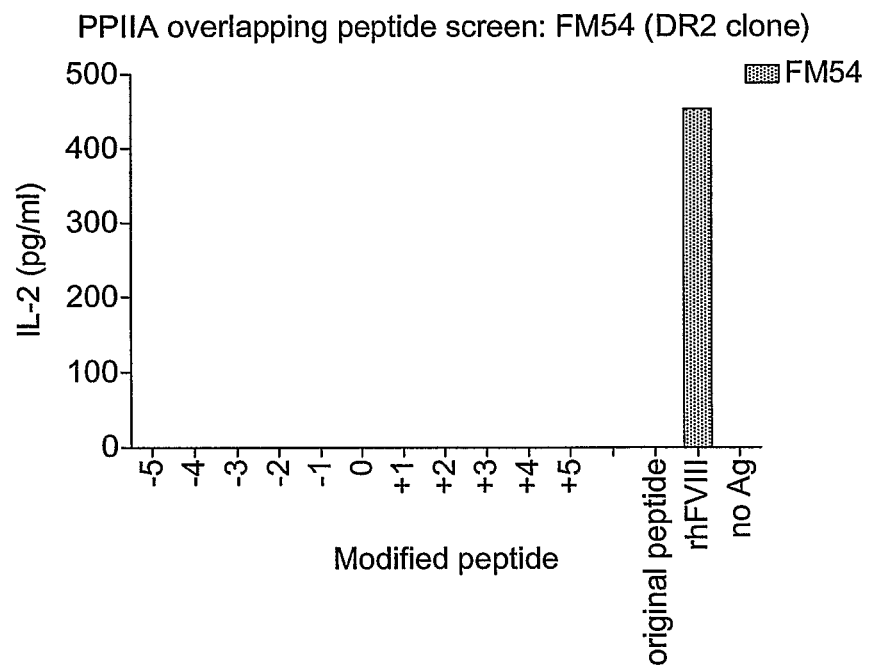
Figure 7C:
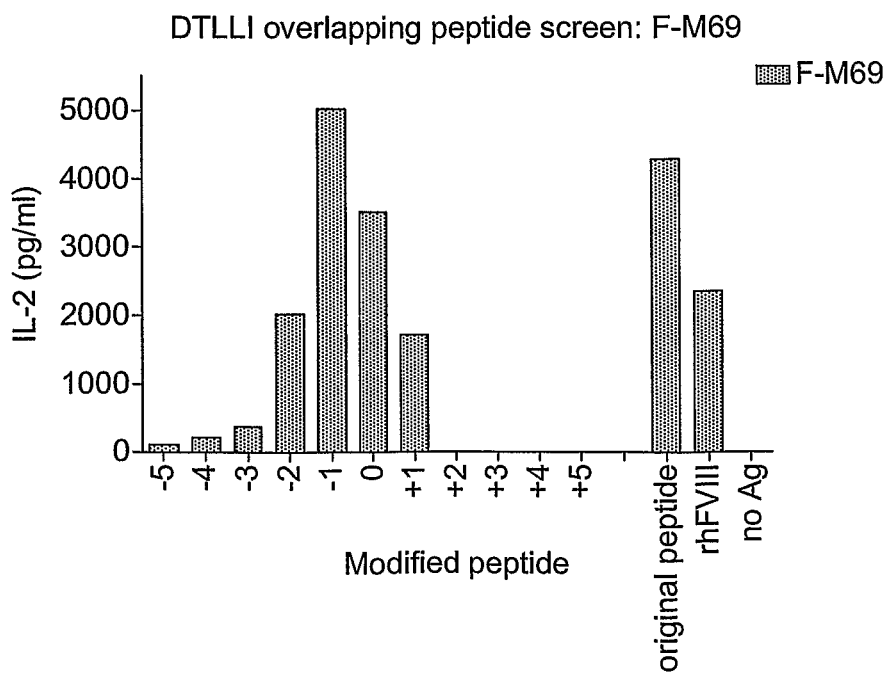
Figure 7C:
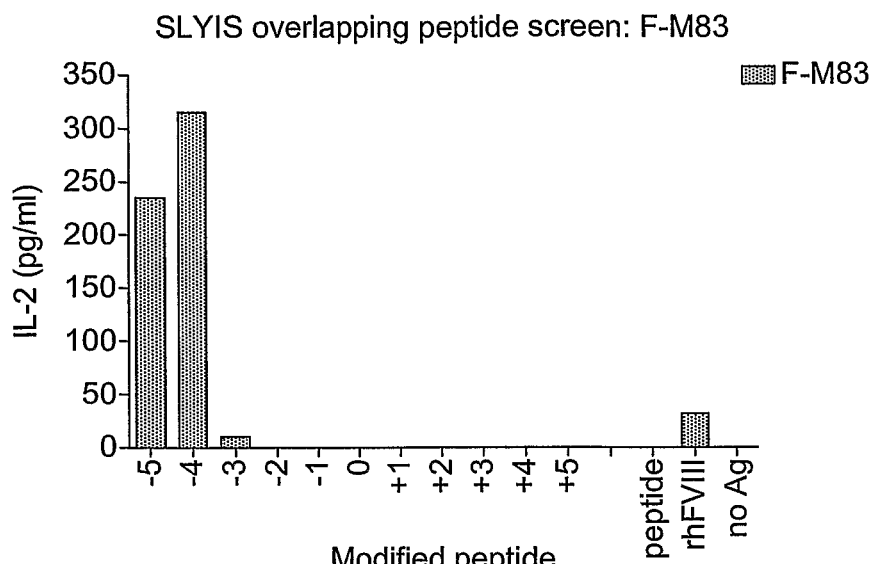
Figure 7C:
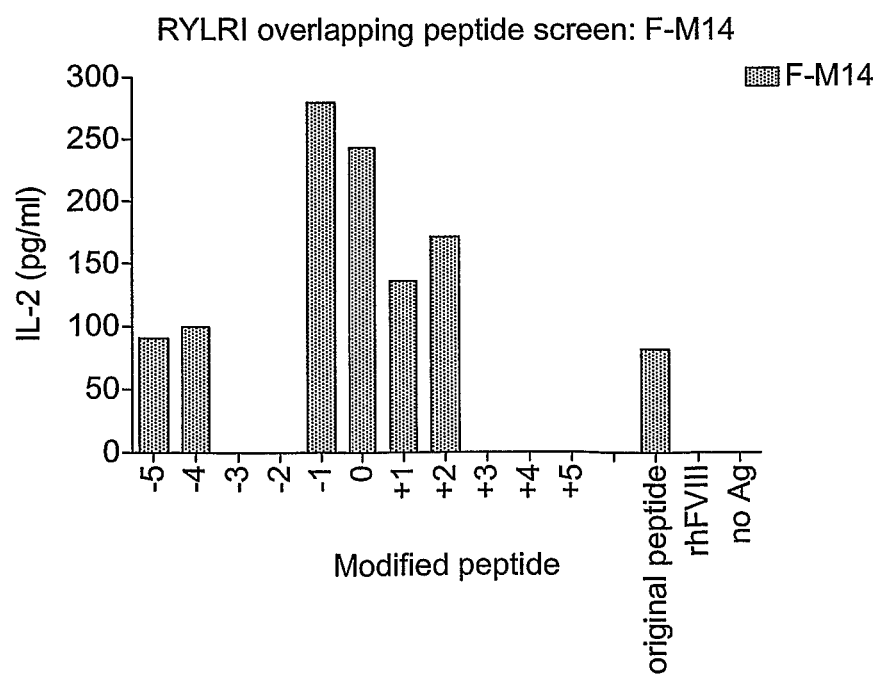

DNIMV (SEQ ID NO:72) and PRCLT (SEQ ID NO:70) Induce Tolerance to Whole Factor VIII Protein HLA-DR2 transgenic mice were treated with either of the two soluble peptides, or PBS as a control, prior to immunisation with factor VIII in adjuvant. Draining lymph nodes were isolated and the cells restimulated in vitro with factor VIII protein in order to assess the immune status of the mice. As shown in FIG. 6, treatment of mice with either DNIMV (SEQ ID NO:72) or PRCLT (SEQ ID NO:70) led to a substantial suppression of the immune response to factor VIII.

Example 9

Investigation of Whether DNIMV (SEQ ID NO:72) and PRCLT (SEQ ID NO:70) Able to Induce Tolerance in the Factor VIII Knockout Mouse It was known from Example 8 that these two peptides are able to prevent the immune response to factor VIII in mice expressing endogenous factor VIII. The experiment was repeated with FVIII-DR2+ animals to determine whether these peptides also prevent the immune response to factor VIII in factor VIII deficient mice.

Example 10

Figure 8:
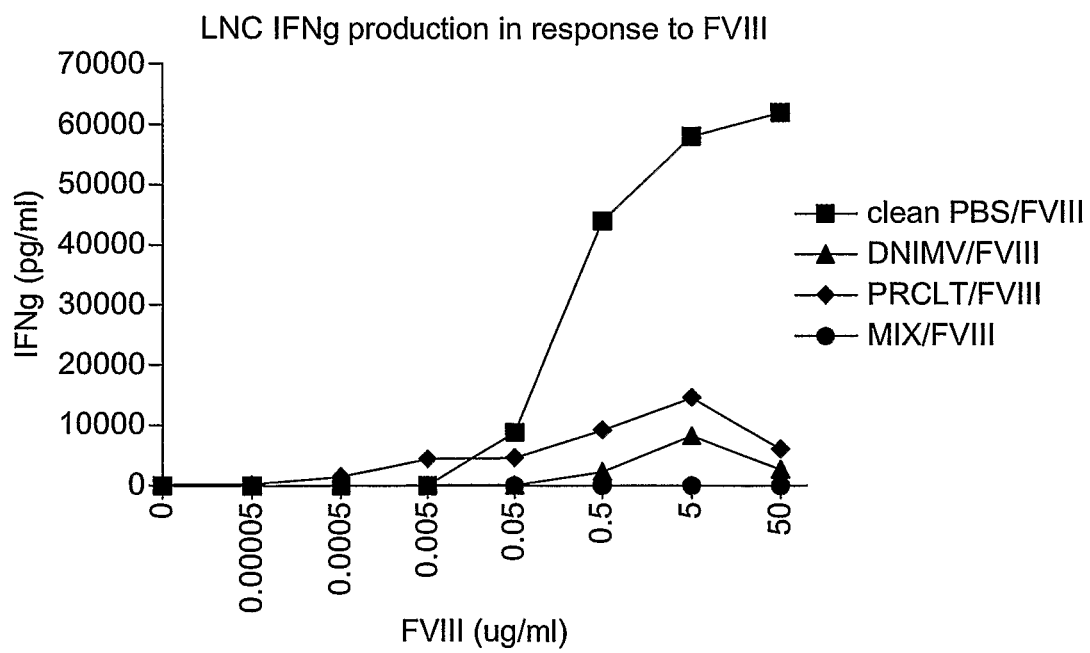

Investigation of Whether DNIMV (SEQ ID NO:72) and PRCLT (SEQ ID NO:70) in Combination are Able to Induce Tolerance in the Factor VIII Knockout Mouse The two peptides which were shown to individually reduce the immune response to factor VIII in factor VIII deficient mice in Example 9 were combined. As shown in FIG. 8, treatment of mice with both DNIMV (SEQ ID NO:72) and PRCLT (SEQ ID NO:70) led to a substantial suppression of the immune response to factor VIII, as shown by the decrease in IFN-gamma production. IFN-gamma is the major class switch lymphokine required for neutralising antibodies in the mouse. The effect demonstrated was greater than that observed using either peptide alone.
Methods
(i) Recall Responses for DR2+ Mice Primed with rhFVIII HLA-DR2+ murine MHC class II null mice were immunised with 40 μg rhFVIII emulsified in Complete Freunds Adjuvant supplemented with 400 μg heat-killed *M. tuberculosis* H37Ra, subcutaneously at the base of the tail. 10 days later the mice were sacrificed and the draining lymph nodes removed. Single cell suspensions were prepared and lymphocytes incubated at 4-5×$10^5$ cells per well in 96-well flat bottomed plates for 72 hours with the indicated concentrations of peptide or control antigens before pulsing with 0.5 μCi/well tritiated thymidine for a further 16 hours. Plates were then frozen before cells were harvested onto glass filter mats and radioactive incorporation measured using a liquid scintillation β-counter
(ii) FVIII Peptide Specificity of T Cell Hybridomas Generated from DR2+ Mice HLA-DR2+ murine MHC class II null mice were immunised as above. On day 10 draining lymph nodes were removed and lymphocytes cultured at 2.5×$10^6$ cells/ml, 1 ml/well in 24 well plates in the presence of 20 μg/ml rhFVIII for 3 days. Following this stimulation, lymphocytes were recovered, washed and fused with TCRα⁻β⁻ BW fusion partner cells at a ratio of 4 BW cells to 1 lymphocyte, using polyethylene glycol as described by Nelson et al (1980) *PNAS* 77(5):2866. Fused cells were carefully washed and then plated out in flat bottomed 96 well plates for 2 days before the addition of HAT medium to select for T cell hybridomas. Cells were monitored for growth and approximately 10 days after fusions were performed, individual clones were selected and transferred to 24 well plates in HAT medium. Clones were maintained in HAT medium for at least 2 weeks before being weaned into HT medium and then complete medium. Clones were tested for antigenic specificity by culturing 100 μl of hybridoma cells with 5×$10^4$ Mgar cells in the presence and absence of 20 μg/ml rhFVIII overnight. Supernatants were then collected and assessed for IL-2 production by ELISA, with clones producing IL-2 in response to rhFVIII being considered positive for FVIII-specificity. To investigate the repertoire of predicted FVIII peptides FVIII-specific clones were again tested for IL-2 production, following overnight incubation with 20 μg/ml of each of the 12 peptides.
(iii) Recall Responses for FVIII−/− Mice Primed with rhFVIII The same method was followed as for (i), except the mice were FVIII-deficient, HLA-DR2+ and murine MHC class II null.
(iv) FVIII Peptide Specificity of T Cell Hybridomas Generated from FVIII−/− Mice The same method was followed as for (ii), except the mice were FVIII-deficient and HLA-DR2+.
(v) Tolerisation of FVIII-Specific Responses in DR2+ Mice by Pre-Treatment with Immunodominant FVIII Peptides HLA-DR2+ murine MHC class II null mice were treated 3 times with 100 μg of DNIMV (SEQ ID NO:72), PRCLT (SEQ ID NO:70) or PPIIA (SEQ ID NO:65) dissolved in PBS, or the equivalent volume of PBS alone. Peptides were administered intraperitoneally, with 3-4 days between each dose. Following the final administration, mice were primed with rhFVIII emulsified in complete Freunds adjuvant as for (i). 10 days later, draining lymph nodes were recovered and lymphocytes subsequently cultured in vitro with rhFVIII, or each of the tolerising peptides as well as control antigens, for 72 hours before the addition of tritiated thymidine as for (i).
(vi) Tolerisation of FVIII-Specific Responses in DR2+ Mice by Pre-Treatment with a Combination Immunodominant FVIII Peptides HLA-DR2+ murine MHC class II null mice were treated 3 times with DNIMV (SEQ ID NO:72), PRCLT (SEQ ID NO:70) or a combination of both DNIMV (SEQ ID NO:72) and PRCLT (SEQ ID NO:70) dissolved in PBS, or the equivalent volume of PBS alone. Peptides were administered intraperitoneally, over 8 days. Following the final administration, mice were primed with rhFVIII emulsified in complete Freunds adjuvant as for (i). 10 days later, draining lymph nodes were recovered and lymphocytes subsequently re-stimulated in vitro with rhFVIII. The supernatants were then collected and IFN-gamma was measured.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments.

Indeed, various modifications of the described modes for carrying out the invention which are obvious to those skilled in cellular studies using flow cytometry or related fields are intended to be within the scope of the following claims.

```
                                                                  SEQ ID No. 1
   1  mqielstcff  lcllrfcfsa  trryylgave  lswdymqsdl  gelpvdarfp  prvpksfpfn
  61  tsvvykktlf  veftdhlfni  akprppwmgl  lgptiqaevy  dtvvitlknm  ashpvslhav
 121  gvsywkaseg  aeyddqtsqr  ekeddkvfpg  gshtyvwqvl  kengpmasdp  lcltysylsh
 181  vdlvkdlnsg  ligallvcre  gslakektqt  lhkfillfav  fdegkswhse  tknslmqdrd
 241  aasarawpkm  htvngyvnrs  lpgligchrk  svywhvigmg  ttpevhsifl  eghtflvrnh
 301  rqasleispi  tfltaqtllm  dlgqfllfch  isshqhdgme  ayvkvdscpe  epqlrmknne
 361  eaedydddlt  dsemdvvrfd  ddnspsfiqi  rsvakkhpkt  wvhyiaaeee  dwdyaplvla
 421  pddrsyksqy  lnngpqrigr  kykkvrfmay  tdetfktrea  iqhesgilgp  Ilygevgdtl
 481  liifknqasr  pyniyphgit  dvrplysrrl  pkgvkhlkdf  pilpgeifky  kwtvtvedgp
 541  tksdprcltr  yyssfvnmer  dlasgligpl  licykesvdq  rgnqimsdkr  nvilfsvfde
 601  nrswylteni  qrflpnpagv  qledpefqas  nimhsingyv  fdslqlsvcl  hevaywyils
 661  igaqtdflsv  ffsgytfkhk  mvyedtltlf  pfsgetvfms  menpglwilg  chnsdfrnrg
 721  mtallkvssc  dkntgdyyed  syedisayll  sknnaieprs  fsqnsrhpst  rqkqfnatti
 781  pendiektdp  wfahrtpmpk  iqnvsssdll  mllrqsptph  glslsdlqea  kyetfsddps
 841  pgaidsnnsl  semthfrpql  hhsgdmvftp  esglqlrine  klgttaatel  kkldfkvsst
 901  snnlistips  dnlaagtdnt  sslgppsmpv  hydsqldttl  fgkkssplte  sggplslsee
 961  nndskllesg  lmnsqesswg  knvsstesgr  lfkgkrahgp  alltkdnalf  kvsisllktn
1021  ktsnnsatnr  kthidgpsll  ienspsvwqn  ilesdtefkk  vtplihdrml  mdknatalrl
1081  nhmsnkttss  knmemvqqkk  egpippdaqn  pdmsffkmlf  lpesarwiqr  thgknslnsg
1141  qgpspkqlvs  lgpeksvegq  nflseknkvv  vgkgeftkdv  glkemvfpss  rnlfltnldn
1201  lhennthnqe  kkiqeeiekk  etliqenvvl  pqihtvtgtk  nfmknlflls  trqnvegsyd
1261  gayapvlqdf  rslndstnrt  kkhtahfskk  geeenleglg  nqtkqiveky  acttrispnt
1321  sqqnfvtqrs  kralkqfrlp  leetelekri  ivddtstqws  knmkhltpst  ltqidyneke
1381  kgaitqspls  dcltrshsip  qanrsplpia  kvssfpsirp  iyltrvlfqd  nsshlpaasy
1441  rkkdsgvqes  shflqgakkn  nlslailtle  mtgdqrevgs  lgtsatnsvt  ykkventvlp
1501  kpdlpktsgk  vellpkvhiy  qkdlfptets  ngspghldlv  egsllqgteg  aikwneanrp
1561  gkvpflrvat  essaktpskl  ldplawdnhy  gtqipkeewk  sqekspekta  fkkkdtilsl
1621  nacesnhaia  ainegqnkpe  ievtwakqgr  terlcsqnpp  vlkrhqreit  rttlqsdqee
1681  idyddtisve  mkkedfdiyd  edenqsprsf  qkktrhyfia  averlwdygm  sssphvlrnr
1741  aqsgsvpqfk  kvvfqeftdg  sftqplyrge  lnehlgllgp  yiraevedni  mvtfrnqasr
1801  pysfysslis  yeedqrqgae  prknfvkpne  tktyfwkvqh  hmaptkdefd  ckawayfsdv
1861  dlekdvhsgl  igpllvchtn  tlnpahgrqv  tvqefalfft  ifdetkswyf  tenmerncra
1921  pcniqmedpt  fkenyrfhai  ngyimdtlpg  lvmaqdqrir  wyllsmgsne  nihsihfsgh
1981  vftvrkkeey  kmalynlypg  vfetvemlps  kagiwrvecl  igehlhagms  tlflvysnkc
2041  qtplgmasgh  irdfqitasg  qygqwapkla  rlhysgsina  wstkepfswi  kvdllapmii
2101  hgiktqgarq  kfsslyisqf  iimysldgkk  wqtyrgnstg  tlmvffgnvd  ssgikhnifn
2161  ppiiaryirl  hpthysirst  lrmewmgcdl  nscsmplgme  skaisdaqit  assyftnmfa
```

```
-continued
2221  twspskarlh lqgrsnawrp qvnnpkewlq vdfqktmkvt gyttqgvksl ltsmyvkefl 2281  isssqdghqw tlffqngkvk vfqgnqdsft pvvnsldppl ltrylrihpq swvhqialrm 2341  evlgceaqdl y
```

Overlapping Peptide Panels Prepared in Example 7

Overlapping set for DTLLIIFKNQASRPY (SEQ ID NO: 13)

```
1.   473-488     YGEVGDTLLIIFKNQ       (SEQ ID NO: 74)

2.   474-489     GEVGDTLLIIFKNQA       (SEQ ID NO: 75)

3.   475-490     EVGDTLLIIFKNQAS       (SEQ ID NO: 76)

4.   476-491     VGDTLLIIFKNQASR       (SEQ ID NO: 77)

5.   477-492     GDTLLIIFKNQASRP       (SEQ ID NO: 78)

6.   478-493     DTLLIIFKNQASRPY       (SEQ ID NO: 13)

7.   479-494     TLLIIFKNQASRPYN       (SEQ ID NO: 34)

8.   480-495     LLIIFKNQASRPYNI       (SEQ ID NO: 33)

9.   481-496     LIIFKNQASRPYNIY       (SEQ ID NO: 32)

10.  482-497     IIFKNQASRPYNIYP       (SEQ ID NO: 79)

11.  483-498     IFKNQASRPYNIYPH       (SEQ ID NO: 80)
```

Overlapping set for PRCLTRYYSSFVNME (SEQ ID NO:9)

```
1.   540-554   PTKSDPRCLTRYYSS       (SEQ ID NO: 81)

2.   541-555   TKSDPRCLTRYYSSF       (SEQ ID NO: 82)

3.   542-556   KSDPRCLTRYYSSFV       (SEQ ID NO: 38)

4.   543-557   SDPRCLTRYYSSFVN       (SEQ ID NO: 39)

5.   544-558   DPRCLTRYYSSFVNM       (SEQ ID NO: 40)

6.   545-559   PRCLTRYYSSFVNME       (SEQ ID NO: 9)

7.   546-560   RCLTRYYSSFVNMER       (SEQ ID NO: 41)

8.   547-561   CLTRYYSSFVNMERD       (SEQ ID NO: 42)

9.   548-562   LTRYYSSFVNMERDL       (SEQ ID NO: 43)

10.  549-563   TRYYSSFVNMERDLA       (SEQ ID NO: 83)

11.  550-564   RYYSSFVNMERDLAS       (SEQ ID NO: 84)
```

Overlapping set for DNIMVTFRNQASRPY (SEQ ID NO:10)

```
1.   1783-1797   RAEVEDNIMVTFRNQ     (SEQ ID NO: 85)

2.   1784-1798   AEVEDNIMVTFRNQA     (SEQ ID NO: 86)

3.   1785-1799   EVEDNIMVTFRNQAS     (SEQ ID NO: 44)

4.   1786-1800   VEDNIMVTFRNQASR     (SEQ ID NO: 45)

5.   1787-1801   EDNIMVTFRNQASRP     (SEQ ID NO: 46)

6.   1788-1802   DNIMVTFRNQASRPY     (SEQ ID NO: 10)

7.   1789-1803   NIMVTFRNQASRPYS     (SEQ ID NO: 47)
```

-continued

| | | | |
|---|---|---|---|
| 8. | 1790-1804 | IMVTFRNQASRPYSF | (SEQ ID NO: 48) |
| 9. | 1791-1805 | MVTFRNQASRPYSFY | (SEQ ID NO: 49) |
| 10. | 1792-1806 | VTFRNQASRPYSFYS | (SEQ ID NO: 87) |
| 11. | 1793-1807 | TFRNQASRPYSFYSS | (SEQ ID NO: 88) |

Overlapping set for SLYISQFIIMYSLDG (SEQ ID NO:11)

| | | | |
|---|---|---|---|
| 1. | 2109-2123 | RQKFSSLYISQFIIM | (SEQ ID NO: 16) |
| 2. | 2110-2124 | QKFSSLYISQFIIMY | (SEQ ID NO: 17) |
| 3. | 2111-2125 | KFSSLYISQFIIMYS | (SEQ ID NO: 18) |
| 4. | 2112-2126 | FSSLYISQFIIMYSL | (SEQ ID NO: 19) |
| 5. | 2113-2127 | SSLYISQFIIMYSLD | (SEQ ID NO: 20) |
| 6. | 2114-2128 | SLYISQFIIMYSLDG | (SEQ ID NO: 11) |
| 7. | 2115-2129 | LYISQFIIMYSLDGK | (SEQ ID NO: 89) |
| 8. | 2116-2130 | YISQFIIMYSLDGKK | (SEQ ID NO: 21) |
| 9. | 2117-2131 | ISQFIIMYSLDGKKW | (SEQ ID NO: 22) |
| 10. | 2118-2132 | SQFIIMYSLDGKKWQ | (SEQ ID NO: 23) |
| 11. | 2119-2133 | QFIIMYSLDGKKWQT | (SEQ ID NO: 24) |

Overlapping set for PPIIARYIRLHPTHY (SEQ ID NO:12)

| | | | |
|---|---|---|---|
| 1. | 2156-2170 | HNIFNPPIIARYIRL | (SEQ ID NO: 90) |
| 2. | 2157-2171 | NIFNPPIIARYIRLH | (SEQ ID NO:91) |
| 3. | 2158-2172 | IFNPPIIARYIRLHP | (SEQ ID NO: 31) |
| 4. | 2159-2173 | FNPPIIARYIRLHPT | (SEQ ID NO: 30) |
| 5. | 2160-2174 | NPPIIARYIRLHPTH | (SEQ ID NO: 29) |
| 6. | 2161-2175 | PPIIARYIRLIIPTHY | (SEQ ID NO: 12) |
| 7. | 2162-2176 | PIIARTYIRLHPTHYS | (SEQ ID NO: 28) |
| 8. | 2163-2177 | IIARYIRLHPTHYSI | (SEQ ID NO: 27) |
| 9. | 2164-2178 | IARYIRLHPTHYSIR | (SEQ ID NO: 26) |
| 10. | 2165-2179 | ARYIRLHPTHYSIRS | (SEQ ID NO: 92) |
| 11. | 2166-2180 | RYIRLHPTHYSIRST | (SEQ ID NO: 93) |

Overlapping set for RYLRIHPQSWVHQIA (SEQ ID NO:14)

| | | | |
|---|---|---|---|
| 1. | 2317-2331 | PPLLTRYLRIHPQSW | (SEQ ID NO: 58) |
| 2. | 2318-2332 | PLLTRYLRHIPQSWV | (SEQ ID NO: 55) |
| 3. | 2319-2333 | LLTRYLRIHPQSWVH | (SEQ ID NO: 54) |
| 4. | 2320-2334 | LTRYLRIHPQSWVHQ | (SEQ ID NO: 53) |
| 5. | 2321-2335 | TRYLRIHPQSWVHQI | (SEQ ID NO: 52) |
| 6. | 2322-2336 | RYLRIHPQSWVHQIA | (SEQ ID NO: 14) |

-continued

| 7. | 2323-2337 | YLRIHPQSWVHQIAL | (SEQ ID NO: 51) |
| 8. | 2324-2338 | LRIHPQSWVHQIALR | (SEQ ID NO: 50) |
| 9. | 2325-2339 | RIEPQSWVHQIALRM | (SEQ ID NO: 94) |
| 10. | 2326-2340 | IHPQSWVHQIALRME | (SEQ ID NO: 95) |
| 11. | 2327-2341 | HPQSWVHQIALRMEV | (SEQ ID NO: 96) |

The invention claimed is:

1. A synthetic peptide consisting of one of the following sequences:
PRCLTRYYSSFVNME (SEQ ID NO: 9),
TKSDPRCLTRYYSSF (SEQ ID NO: 82),
KSDPRCLTRYYSSFV (SEQ ID NO: 38),
SDPRCLTRYYSSFVN (SEQ ID NO: 39),
DPRCLTRYYSSFVNM (SEQ ID NO: 40),
RCLTRYYSSFVNMER (SEQ ID NO: 41),
CLTRYYSSFVNMERD (SEQ ID NO: 42),
VEDNIMVTFRNQASR (SEQ ID NO: 45),
DNIMVTFRNQASRPY (SEQ ID NO: 10),
IMVTFRNQASRPYSF (SEQ ID NO: 48),
MVTFRNQASRPYSFY (SEQ ID NO: 49),
VTFRNQASRPYSFYS (SEQ ID NO: 87),
PPIIARYIRLHPTHY (SEQ ID NO: 12),
PIIARYIRLHPTHYS (SEQ ID NO: 28),
ARYIRLHPTHYSIRS (SEQ ID NO: 92),
GDTLLIIFKNQASRP (SEQ ID NO: 78),
DTLLIIFKNQASRPY (SEQ ID NO: 13),
TLLIIFKNQASRPYN (SEQ ID NO: 34),
RQKFSSLYISQFIIM (SEQ ID NO: 16),
QKFSSLYISQFIIMY (SEQ ID NO: 17),
PPLLTRYLRIHPQSW (SEQ ID NO: 58),
PLLTRYLRIHPQSWV (SEQ ID NO: 55),
RYLRIHPQSWVHQIA (SEQ ID NO: 14),
YLRIHPQSWVHQIAL (SEQ ID NO: 51),
LRIHPQSWVHQIALR (SEQ ID NO: 50).

2. A composition comprising a plurality of the synthetic peptides according to claim 1.

3. The synthetic peptide according to claim 1 capable of suppressing the production of factor VIII inhibitor antibodies in vivo.

4. A method for suppressing the production of factor VIII inhibitor antibodies in a subject, which comprises the step of administering the synthetic peptide of claim 1, to the subject in need thereof.

5. A method for treating haemophilia in a subject which comprises the step of administering the synthetic peptide of claim 1, to the subject in need thereof.

6. The method according to claim 4, wherein the subject has haemophilia A, and is undergoing, or is about to undergo, factor VIII replacement therapy.

7. The method according to claim 4, wherein the subject has, or is at risk from contracting, acquired haemophilia.

8. The method according to claim 4, wherein the subject is HLA-DR2 positive.

* * * * *

SEQUENCE LISTING

<160> NUMBER OF SEQ ID NOS: 96

<210> SEQ ID NO 1
<211> LENGTH: 2351
<212> TYPE: PRT
<213> ORGANISM: Homo sapiens

<400> SEQUENCE: 1

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser

```
                   290                 295                 300
Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
                355                 360                 365

Leu Thr Asp Ser Glu Met Asp Val Val Arg Phe Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
                435                 440                 445

Ala Tyr Thr Asp Glu Thr Phe Lys Thr Arg Glu Ala Ile Gln His Glu
                450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
                515                 520                 525

Lys Tyr Lys Trp Thr Val Thr Val Glu Asp Gly Pro Thr Lys Ser Asp
                530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
                610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
                690                 695                 700

Gly Leu Trp Ile Leu Gly Cys His Asn Ser Asp Phe Arg Asn Arg Gly
705                 710                 715                 720
```

```
Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
785                 790                 795                 800

Ile Gln Asn Val Ser Ser Asp Leu Leu Met Leu Leu Arg Gln Ser
            805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
            850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
            930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
                995                 1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Lys Lys Val Thr Pro Leu Ile His Asp Arg
    1055                1060                1065

Met Leu Met Asp Lys Asn Ala Thr Ala Leu Arg Leu Asn His Met
    1070                1075                1080

Ser Asn Lys Thr Thr Ser Ser Lys Asn Met Glu Met Val Gln Gln
    1085                1090                1095

Lys Lys Glu Gly Pro Ile Pro Pro Asp Ala Gln Asn Pro Asp Met
    1100                1105                1110

Ser Phe Phe Lys Met Leu Phe Leu Pro Glu Ser Ala Arg Trp Ile
    1115                1120                1125

Gln Arg Thr His Gly Lys Asn Ser Leu Asn Ser Gly Gln Gly Pro
    1130                1135                1140
```

```
Ser Pro Lys Gln Leu Val  Ser Leu Gly Pro Glu  Lys Ser Val Glu
1145              1150              1155

Gly Gln Asn Phe Leu Ser  Glu Lys Asn Lys Val  Val Val Gly Lys
1160              1165              1170

Gly Glu Phe Thr Lys Asp  Val Gly Leu Lys Glu  Met Val Phe Pro
1175              1180              1185

Ser Ser Arg Asn Leu Phe  Leu Thr Asn Leu Asp  Asn Leu His Glu
1190              1195              1200

Asn Asn Thr His Asn Gln  Glu Lys Lys Ile Gln  Glu Glu Ile Glu
1205              1210              1215

Lys Lys Glu Thr Leu Ile  Gln Glu Asn Val Val  Leu Pro Gln Ile
1220              1225              1230

His Thr Val Thr Gly Thr  Lys Asn Phe Met Lys  Asn Leu Phe Leu
1235              1240              1245

Leu Ser Thr Arg Gln Asn  Val Glu Gly Ser Tyr  Asp Gly Ala Tyr
1250              1255              1260

Ala Pro Val Leu Gln Asp  Phe Arg Ser Leu Asn  Asp Ser Thr Asn
1265              1270              1275

Arg Thr Lys Lys His Thr  Ala His Phe Ser Lys  Lys Gly Glu Glu
1280              1285              1290

Glu Asn Leu Glu Gly Leu  Gly Asn Gln Thr Lys  Gln Ile Val Glu
1295              1300              1305

Lys Tyr Ala Cys Thr Thr  Arg Ile Ser Pro Asn  Thr Ser Gln Gln
1310              1315              1320

Asn Phe Val Thr Gln Arg  Ser Lys Arg Ala Leu  Lys Gln Phe Arg
1325              1330              1335

Leu Pro Leu Glu Glu Thr  Glu Leu Glu Lys Arg  Ile Ile Val Asp
1340              1345              1350

Asp Thr Ser Thr Gln Trp  Ser Lys Asn Met Lys  His Leu Thr Pro
1355              1360              1365

Ser Thr Leu Thr Gln Ile  Asp Tyr Asn Glu Lys  Glu Lys Gly Ala
1370              1375              1380

Ile Thr Gln Ser Pro Leu  Ser Asp Cys Leu Thr  Arg Ser His Ser
1385              1390              1395

Ile Pro Gln Ala Asn Arg  Ser Pro Leu Pro Ile  Ala Lys Val Ser
1400              1405              1410

Ser Phe Pro Ser Ile Arg  Pro Ile Tyr Leu Thr  Arg Val Leu Phe
1415              1420              1425

Gln Asp Asn Ser Ser His  Leu Pro Ala Ala Ser  Tyr Arg Lys Lys
1430              1435              1440

Asp Ser Gly Val Gln Glu  Ser Ser His Phe Leu  Gln Gly Ala Lys
1445              1450              1455

Lys Asn Asn Leu Ser Leu  Ala Ile Leu Thr Leu  Glu Met Thr Gly
1460              1465              1470

Asp Gln Arg Glu Val Gly  Ser Leu Gly Thr Ser  Ala Thr Asn Ser
1475              1480              1485

Val Thr Tyr Lys Lys Val  Glu Asn Thr Val Leu  Pro Lys Pro Asp
1490              1495              1500

Leu Pro Lys Thr Ser Gly  Lys Val Glu Leu Leu  Pro Lys Val His
1505              1510              1515

Ile Tyr Gln Lys Asp Leu  Phe Pro Thr Glu Thr  Ser Asn Gly Ser
1520              1525              1530

Pro Gly His Leu Asp Leu  Val Glu Gly Ser Leu  Leu Gln Gly Thr
```

-continued

```
                    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785

Asn Ile Met Val Thr Phe Arg Asn Gln Ala Ser Arg Pro Tyr Ser
    1790                1795                1800

Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830

Tyr Phe Trp Lys Val Gln His His Met Ala Pro Thr Lys Asp Glu
    1835                1840                1845

Phe Asp Cys Lys Ala Trp Ala Tyr Phe Ser Asp Val Asp Leu Glu
    1850                1855                1860

Lys Asp Val His Ser Gly Leu Ile Gly Pro Leu Leu Val Cys His
    1865                1870                1875

Thr Asn Thr Leu Asn Pro Ala His Gly Arg Gln Val Thr Val Gln
    1880                1885                1890

Glu Phe Ala Leu Phe Phe Thr Ile Phe Asp Glu Thr Lys Ser Trp
    1895                1900                1905

Tyr Phe Thr Glu Asn Met Glu Arg Asn Cys Arg Ala Pro Cys Asn
    1910                1915                1920

Ile Gln Met Glu Asp Pro Thr Phe Lys Glu Asn Tyr Arg Phe His
    1925                1930                1935
```

```
Ala Ile Asn Gly Tyr Ile Met Asp Thr Leu Pro Gly Leu Val Met
1940                1945                1950

Ala Gln Asp Gln Arg Ile Arg Trp Tyr Leu Leu Ser Met Gly Ser
1955                1960                1965

Asn Glu Asn Ile His Ser Ile His Phe Ser Gly His Val Phe Thr
1970                1975                1980

Val Arg Lys Lys Glu Glu Tyr Lys Met Ala Leu Tyr Asn Leu Tyr
1985                1990                1995

Pro Gly Val Phe Glu Thr Val Glu Met Leu Pro Ser Lys Ala Gly
2000                2005                2010

Ile Trp Arg Val Glu Cys Leu Ile Gly Glu His Leu His Ala Gly
2015                2020                2025

Met Ser Thr Leu Phe Leu Val Tyr Ser Asn Lys Cys Gln Thr Pro
2030                2035                2040

Leu Gly Met Ala Ser Gly His Ile Arg Asp Phe Gln Ile Thr Ala
2045                2050                2055

Ser Gly Gln Tyr Gly Gln Trp Ala Pro Lys Leu Ala Arg Leu His
2060                2065                2070

Tyr Ser Gly Ser Ile Asn Ala Trp Ser Thr Lys Glu Pro Phe Ser
2075                2080                2085

Trp Ile Lys Val Asp Leu Leu Ala Pro Met Ile Ile His Gly Ile
2090                2095                2100

Lys Thr Gln Gly Ala Arg Gln Lys Phe Ser Ser Leu Tyr Ile Ser
2105                2110                2115

Gln Phe Ile Ile Met Tyr Ser Leu Asp Gly Lys Lys Trp Gln Thr
2120                2125                2130

Tyr Arg Gly Asn Ser Thr Gly Thr Leu Met Val Phe Phe Gly Asn
2135                2140                2145

Val Asp Ser Ser Gly Ile Lys His Asn Ile Phe Asn Pro Pro Ile
2150                2155                2160

Ile Ala Arg Tyr Ile Arg Leu His Pro Thr His Tyr Ser Ile Arg
2165                2170                2175

Ser Thr Leu Arg Met Glu Trp Met Gly Cys Asp Leu Asn Ser Cys
2180                2185                2190

Ser Met Pro Leu Gly Met Glu Ser Lys Ala Ile Ser Asp Ala Gln
2195                2200                2205

Ile Thr Ala Ser Ser Tyr Phe Thr Asn Met Phe Ala Thr Trp Ser
2210                2215                2220

Pro Ser Lys Ala Arg Leu His Leu Gln Gly Arg Ser Asn Ala Trp
2225                2230                2235

Arg Pro Gln Val Asn Asn Pro Lys Glu Trp Leu Gln Val Asp Phe
2240                2245                2250

Gln Lys Thr Met Lys Val Thr Gly Val Thr Thr Gln Gly Val Lys
2255                2260                2265

Ser Leu Leu Thr Ser Met Tyr Val Lys Glu Phe Leu Ile Ser Ser
2270                2275                2280

Ser Gln Asp Gly His Gln Trp Thr Leu Phe Phe Gln Asn Gly Lys
2285                2290                2295

Val Lys Val Phe Gln Gly Asn Gln Asp Ser Phe Thr Pro Val Val
2300                2305                2310

Asn Ser Leu Asp Pro Pro Leu Leu Thr Arg Tyr Leu Arg Ile His
2315                2320                2325

Pro Gln Ser Trp Val His Gln Ile Ala Leu Arg Met Glu Val Leu
2330                2335                2340
```

```
Gly Cys  Glu Ala Gln Asp Leu  Tyr
    2345                2350

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Leu Tyr Ile Ser Gln Phe Ile Ile Met
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Phe Ile Ile Met Tyr Ser Leu Asp Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Ile Ala Arg Tyr Ile Arg Leu His Pro
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Leu Ile Ile Phe Lys Asn Gln Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Leu Thr Arg Tyr Tyr Ser Ser Phe Val
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Met Val Thr Phe Arg Asn Gln Ala Ser
```

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Leu Arg Ile His Pro Gln Ser Trp Val
1               5

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide

<400> SEQUENCE: 9

Pro Arg Cys Leu Thr Arg Tyr Tyr Ser Ser Phe Val Asn Met Glu
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide

<400> SEQUENCE: 10

Asp Asn Ile Met Val Thr Phe Arg Asn Gln Ala Ser Arg Pro Tyr
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

Ser Leu Tyr Ile Ser Gln Phe Ile Ile Met Tyr Ser Leu Asp Gly
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide

<400> SEQUENCE: 12

Pro Pro Ile Ile Ala Arg Tyr Ile Arg Leu His Pro Thr His Tyr
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide

<400> SEQUENCE: 13

Asp Thr Leu Leu Ile Ile Phe Lys Asn Gln Ala Ser Arg Pro Tyr
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic peptide

<400> SEQUENCE: 14

Arg Tyr Leu Arg Ile His Pro Gln Ser Trp Val His Gln Ile Ala
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide

<400> SEQUENCE: 15

Leu Tyr Ile Ser Gln Phe Ile Ile Met Met Tyr Ser Leu Asp Gly Lys
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide

<400> SEQUENCE: 16

Arg Gln Lys Phe Ser Ser Leu Tyr Ile Ser Gln Phe Ile Ile Met
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic peptide

<400> SEQUENCE: 17

Gln Lys Phe Ser Ser Leu Tyr Ile Ser Gln Phe Ile Ile Met Tyr
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic peptide

<400> SEQUENCE: 18

Lys Phe Ser Ser Leu Tyr Ile Ser Gln Phe Ile Ile Met Tyr Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Phe Ser Ser Leu Tyr Ile Ser Gln Phe Ile Ile Met Tyr Ser Leu
1               5                   10                  15

<210> SEQ ID NO 20

```
<211> LENGTH: 15
<212> TYPE: PRT
<213> ORGANISM: Artificial Sequence
<220> FEATURE:
<223> OTHER INFORMATION: Synthetic peptide

<400> SEQUENCE: 20

Ser Ser Leu Tyr Ile Ser Gln Phe Ile Ile Met Tyr Ser Leu Asp
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide

<400> SEQUENCE: 21

Tyr Ile Ser Gln Phe Ile Ile Met Tyr Ser Leu Asp Gly Lys Lys
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide

<400> SEQUENCE: 22

Ile Ser Gln Phe Ile Ile Met Tyr Ser Leu Asp Gly Lys Lys Trp
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide

<400> SEQUENCE: 23

Ser Gln Phe Ile Ile Met Tyr Ser Leu Asp Gly Lys Lys Trp Gln
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide

<400> SEQUENCE: 24

Gln Phe Ile Ile Met Tyr Ser Leu Asp Gly Lys Lys Trp Gln Thr
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide

<400> SEQUENCE: 25

Phe Ile Ile Met Tyr Ser Leu Asp Gly Lys Lys Trp Gln Thr Tyr
1               5                   10                  15

<210> SEQ ID NO 26
<211> LENGTH: 15
<212> TYPE: PRT
```

<213> ORGANISM: Artificial Sequence
<220> FEATURE:
<223> OTHER INFORMATION: Synthetic peptide

<400> SEQUENCE: 26

Ile Ala Arg Tyr Ile Arg Leu His Pro Thr His Tyr Ser Ile Arg
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide

<400> SEQUENCE: 27

Ile Ile Ala Arg Tyr Ile Arg Leu His Pro Thr His Tyr Ser Ile
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic peptide

<400> SEQUENCE: 28

Pro Ile Ile Ala Arg Tyr Ile Arg Leu His Pro Thr His Tyr Ser
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic peptide

<400> SEQUENCE: 29

Asn Pro Pro Ile Ile Ala Arg Tyr Ile Arg Leu His Pro Thr His
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic peptide

<400> SEQUENCE: 30

Phe Asn Pro Pro Ile Ile Ala Arg Tyr Ile Arg Leu His Pro Thr
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic peptide

<400> SEQUENCE: 31

Ile Phe Asn Pro Pro Ile Ile Ala Arg Tyr Ile Arg Leu His Pro
1               5                   10                  15

<210> SEQ ID NO 32
<211> LENGTH: 15
<212> TYPE: PRT
<213> ORGANISM: Artificial Sequence
<220> FEATURE:

```
<223> OTHER INFORMATION: Synthetic peptide

<400> SEQUENCE: 32

Leu Ile Ile Phe Lys Asn Gln Ala Ser Arg Pro Tyr Asn Ile Tyr
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic peptide

<400> SEQUENCE: 33

Leu Leu Ile Ile Phe Lys Asn Gln Ala Ser Arg Pro Tyr Asn Ile
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic peptide

<400> SEQUENCE: 34

Thr Leu Leu Ile Ile Phe Lys Asn Gln Ala Ser Arg Pro Tyr Asn
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Synthetic peptide

<400> SEQUENCE: 35

Gly Asp Thr Leu Leu Leu Ile Ile Phe Lys Asn Gln Ala Ser Arg Pro
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetic peptide

<400> SEQUENCE: 36

Val Gly Asp Thr Leu Leu Leu Ile Ile Phe Lys Asn Gln Ala Ser Arg
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Synthetic peptide

<400> SEQUENCE: 37

Glu Val Gly Asp Thr Leu Leu Leu Ile Ile Phe Lys Asn Gln Ala Ser
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic peptide
```

```
<400> SEQUENCE: 38

Lys Ser Asp Pro Arg Cys Leu Thr Arg Tyr Tyr Ser Ser Phe Val
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Synthetic peptide

<400> SEQUENCE: 39

Ser Asp Pro Arg Cys Leu Thr Arg Tyr Tyr Ser Ser Phe Val Asn
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic peptide

<400> SEQUENCE: 40

Asp Pro Arg Cys Leu Thr Arg Tyr Tyr Ser Ser Phe Val Asn Met
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic peptide

<400> SEQUENCE: 41

Arg Cys Leu Thr Arg Tyr Tyr Ser Ser Phe Val Asn Met Glu Arg
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic peptide

<400> SEQUENCE: 42

Cys Leu Thr Arg Tyr Tyr Ser Ser Phe Val Asn Met Glu Arg Asp
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Synthetic peptide

<400> SEQUENCE: 43

Leu Thr Arg Tyr Tyr Ser Ser Phe Val Asn Met Glu Arg Asp Leu
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic peptide

<400> SEQUENCE: 44
```

-continued

```
Glu Val Glu Asp Asn Ile Met Val Thr Phe Arg Asn Gln Ala Ser
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Synthetic peptide

<400> SEQUENCE: 45

Val Glu Asp Asn Ile Met Val Thr Phe Arg Asn Gln Ala Ser Arg
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic peptide

<400> SEQUENCE: 46

Glu Asp Asn Ile Met Val Thr Phe Arg Asn Gln Ala Ser Arg Pro
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic peptide

<400> SEQUENCE: 47

Asn Ile Met Val Thr Phe Arg Asn Gln Ala Ser Arg Pro Tyr Ser
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic peptide

<400> SEQUENCE: 48

Ile Met Val Thr Phe Arg Asn Gln Ala Ser Arg Pro Tyr Ser Phe
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic peptide

<400> SEQUENCE: 49

Met Val Thr Phe Arg Asn Gln Ala Ser Arg Pro Tyr Ser Phe Tyr
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic peptide

<400> SEQUENCE: 50

Leu Arg Ile His Pro Gln Ser Trp Val His Gln Ile Ala Leu Arg
1               5                   10                  15
```

```
<210> SEQ ID NO 51
<211> LENGTH: 15
<212> TYPE: PRT
<213> ORGANISM: Artificial Sequence
<220> FEATURE:
<223> OTHER INFORMATION: Synthetic peptide

<400> SEQUENCE: 51

Tyr Leu Arg Ile His Pro Gln Ser Trp Val His Gln Ile Ala Leu
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic peptide

<400> SEQUENCE: 52

Thr Arg Tyr Leu Arg Ile His Pro Gln Ser Trp Val His Gln Ile
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic peptide

<400> SEQUENCE: 53

Leu Thr Arg Tyr Leu Arg Ile His Pro Gln Ser Trp Val His Gln
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic peptide

<400> SEQUENCE: 54

Leu Leu Thr Arg Tyr Leu Arg Ile His Pro Gln Ser Trp Val His
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic peptide

<400> SEQUENCE: 55

Pro Leu Leu Thr Arg Tyr Leu Arg Ile His Pro Gln Ser Trp Val
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic peptide

<400> SEQUENCE: 56

Gly Thr Leu Met Val Phe Phe Gly Asn Val Asp Ser Ser Gly Ile
1               5                   10                  15
```

```
<210> SEQ ID NO 57
<211> LENGTH: 15
<212> TYPE: PRT
<213> ORGANISM: Artificial Sequence
<220> FEATURE:
<223> OTHER INFORMATION: Synthetic peptide

<400> SEQUENCE: 57

Thr Gln Thr Leu His Lys Phe Ile Leu Leu Phe Ala Val Phe Asp
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Synthetic peptide

<400> SEQUENCE: 58

Pro Pro Leu Leu Thr Arg Tyr Leu Arg Ile His Pro Gln Ser Trp
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic peptide

<400> SEQUENCE: 59

Met His Thr Val Asn Gly Tyr Val Asn Arg Ser Leu Pro Gly Leu
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic peptide

<400> SEQUENCE: 60

Leu Gly Gln Phe Leu Leu Phe Cys His Ile Ser Ser His Gln His
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic peptide

<400> SEQUENCE: 61

Thr Glu Asn Ile Gln Arg Phe Leu Pro Asn Pro Ala Gly Val Gln
1               5                   10                  15

<210> SEQ ID NO 62
<211> LENGTH: 5
<212> TYPE: PRT
<213> ORGANISM: Artificial Sequence
<220> FEATURE:
<223> OTHER INFORMATION: Synthetic peptide

<400> SEQUENCE: 62

Gly Thr Leu Met Val
1               5

<210> SEQ ID NO 63
<211> LENGTH: 5
```

```
<212> TYPE: PRT
<213> ORGANISM: Artificial Sequence
<220> FEATURE:
<223> OTHER INFORMATION: Synthetic peptide

<400> SEQUENCE: 63

Thr Gln Thr Leu His
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic peptide

<400> SEQUENCE: 64

Ser Leu Tyr Ile Ser
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic peptide

<400> SEQUENCE: 65

Pro Pro Ile Ile Ala
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic peptide

<400> SEQUENCE: 66

Pro Pro Leu Leu Thr
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic peptide

<400> SEQUENCE: 67

Met His Thr Val Asn
1               5

<210> SEQ ID NO 68
<211> LENGTH: 5
<212> TYPE: PRT
<213> ORGANISM: Artificial Sequence
<220> FEATURE:
<223> OTHER INFORMATION: Synthetic peptide

<400> SEQUENCE: 68

Leu Gly Gln Phe Leu
1               5

<210> SEQ ID NO 69
<211> LENGTH: 5
<212> TYPE: PRT
<213> ORGANISM: Artificial Sequence
```

```
<220> FEATURE:
<223> OTHER INFORMATION: Synthetic peptide

<400> SEQUENCE: 69

Asp Thr Leu Leu Ile
1               5

<210> SEQ ID NO 70
<211> LENGTH: 5
<212> TYPE: PRT
<213> ORGANISM: Artificial Sequence
<220> FEATURE:
<223> OTHER INFORMATION: Synthetic peptide

<400> SEQUENCE: 70

Pro Arg Cys Leu Thr
1               5

<210> SEQ ID NO 71
<211> LENGTH: 5
<212> TYPE: PRT
<213> ORGANISM: Artificial Sequence
<220> FEATURE:
<223> OTHER INFORMATION: Synthetic peptide

<400> SEQUENCE: 71

Thr Glu Asn Ile Gln
1               5

<210> SEQ ID NO 72
<211> LENGTH: 5
<212> TYPE: PRT
<213> ORGANISM: Artificial Sequence
<220> FEATURE:
<223> OTHER INFORMATION: Synthetic peptide

<400> SEQUENCE: 72

Asp Asn Ile Met Val
1               5

<210> SEQ ID NO 73
<211> LENGTH: 5
<212> TYPE: PRT
<213> ORGANISM: Artificial Sequence
<220> FEATURE:
<223> OTHER INFORMATION: Synthetic peptide

<400> SEQUENCE: 73

Arg Tyr Leu Arg Ile
1               5

<210> SEQ ID NO 74
<211> LENGTH: 15
<212> TYPE: PRT
<213> ORGANISM: Artificial Sequence
<220> FEATURE:
<223> OTHER INFORMATION: Synthetic peptide

<400> SEQUENCE: 74

Tyr Gly Glu Val Gly Asp Thr Leu Leu Ile Ile Phe Lys Asn Gln
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Synthetic peptide
```

-continued

<400> SEQUENCE: 75

Gly Glu Val Gly Asp Thr Leu Leu Ile Ile Phe Lys Asn Gln Ala
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic peptide

<400> SEQUENCE: 76

Glu Val Gly Asp Thr Leu Leu Ile Ile Phe Lys Asn Gln Ala Ser
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Synthetic peptide

<400> SEQUENCE: 77

Val Gly Asp Thr Leu Leu Ile Ile Phe Lys Asn Gln Ala Ser Arg
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic peptide

<400> SEQUENCE: 78

Gly Asp Thr Leu Leu Ile Ile Phe Lys Asn Gln Ala Ser Arg Pro
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic peptide

<400> SEQUENCE: 79

Ile Ile Phe Lys Asn Gln Ala Ser Arg Pro Tyr Asn Ile Tyr Pro
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic peptide

<400> SEQUENCE: 80

Ile Phe Lys Asn Gln Ala Ser Arg Pro Tyr Asn Ile Tyr Pro His
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Synthetic peptide

<400> SEQUENCE: 81

```
Pro Thr Lys Ser Asp Pro Arg Cys Leu Thr Arg Tyr Tyr Ser Ser
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic peptide

<400> SEQUENCE: 82

Thr Lys Ser Asp Pro Arg Cys Leu Thr Arg Tyr Tyr Ser Ser Phe
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Synthetic peptide

<400> SEQUENCE: 83

Thr Arg Tyr Tyr Ser Ser Phe Val Asn Met Glu Arg Asp Leu Ala
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Synthetic peptide

<400> SEQUENCE: 84

Arg Tyr Tyr Ser Ser Phe Val Asn Met Glu Arg Asp Leu Ala Ser
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic peptide

<400> SEQUENCE: 85

Arg Ala Glu Val Glu Asp Asn Ile Met Val Thr Phe Arg Asn Gln
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic peptide

<400> SEQUENCE: 86

Ala Glu Val Glu Asp Asn Ile Met Val Thr Phe Arg Asn Gln Ala
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Synthetic peptide

<400> SEQUENCE: 87

Val Thr Phe Arg Asn Gln Ala Ser Arg Pro Tyr Ser Phe Tyr Ser
```

```
                1               5                   10                  15
```

<210> SEQ ID NO 88
<211> LENGTH: 15
<212> TYPE: PRT
<213> ORGANISM: Artificial Sequence
<220> FEATURE:
<223> OTHER INFORMATION: Synthetic peptide

<400> SEQUENCE: 88

```
Thr Phe Arg Asn Gln Ala Ser Arg Pro Tyr Ser Phe Tyr Ser Ser
1               5                   10                  15
```

<210> SEQ ID NO 89
<211> LENGTH: 15
<212> TYPE: PRT
<213> ORGANISM: Artificial Sequence
<220> FEATURE:
<223> OTHER INFORMATION: Synthetic peptide

<400> SEQUENCE: 89

```
Leu Tyr Ile Ser Gln Phe Ile Ile Met Tyr Ser Leu Asp Gly Lys
1               5                   10                  15
```

<210> SEQ ID NO 90
<211> LENGTH: 15
<212> TYPE: PRT
<213> ORGANISM: Artificial Sequence
<220> FEATURE:
<223> OTHER INFORMATION: Synthetic peptide

<400> SEQUENCE: 90

```
His Asn Ile Phe Asn Pro Pro Ile Ile Ala Arg Tyr Ile Arg Leu
1               5                   10                  15
```

<210> SEQ ID NO 91
<211> LENGTH: 15
<212> TYPE: PRT
<213> ORGANISM: Artificial Sequence
<220> FEATURE:
<223> OTHER INFORMATION: Synthetic peptide

<400> SEQUENCE: 91

```
Asn Ile Phe Asn Pro Pro Ile Ile Ala Arg Tyr Ile Arg Leu His
1               5                   10                  15
```

<210> SEQ ID NO 92
<211> LENGTH: 15
<212> TYPE: PRT
<213> ORGANISM: Artificial Sequence
<220> FEATURE:
<223> OTHER INFORMATION: Synthetic peptide

<400> SEQUENCE: 92

```
Ala Arg Tyr Ile Arg Leu His Pro Thr His Tyr Ser Ile Arg Ser
1               5                   10                  15
```

<210> SEQ ID NO 93
<211> LENGTH: 15
<212> TYPE: PRT
<213> ORGANISM: Artificial Sequence
<220> FEATURE:
<223> OTHER INFORMATION: Synthetic peptide

<400> SEQUENCE: 93

```
Arg Tyr Ile Arg Leu His Pro Thr His Tyr Ser Ile Arg Ser Thr
1               5                   10                  15
```

```
<210> SEQ ID NO 94
<211> LENGTH: 15
<212> TYPE: PRT
<213> ORGANISM: Artificial Sequence
<220> FEATURE:
<223> OTHER INFORMATION: Synthetic peptide

<400> SEQUENCE: 94

Arg Ile His Pro Gln Ser Trp Val His Gln Ile Ala Leu Arg Met
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic peptide

<400> SEQUENCE: 95

Ile His Pro Gln Ser Trp Val His Gln Ile Ala Leu Arg Met Glu
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Synthetic peptide

<400> SEQUENCE: 96

His Pro Gln Ser Trp Val His Gln Ile Ala Leu Arg Met Glu Val
1               5                   10                  15
```